US011203627B2

(12) United States Patent
Hayes et al.

(10) Patent No.: US 11,203,627 B2
(45) Date of Patent: Dec. 21, 2021

(54) T CELL RECEPTORS

(71) Applicant: Adaptimmune Limited, Abingdon (GB)

(72) Inventors: Conor Hayes, Abingdon (GB); Arsen Volkov, Abingdon (GB); Andrew Gerry, Abingdon (GB); Ellen Border, Abingdon (GB); Edward Carter, Abindgon (GB)

(73) Assignee: ADAPTIMMUNE LIMITED, Abingdon (GB)

( * ) Notice: Subject to any disclaimer, the term of this patent is extended or adjusted under 35 U.S.C. 154(b) by 584 days.

(21) Appl. No.: 15/480,103

(22) Filed: Apr. 5, 2017

(65) Prior Publication Data

US 2017/0218043 A1 Aug. 3, 2017
US 2018/0208638 A9 Jul. 26, 2018

Related U.S. Application Data

(63) Continuation-in-part of application No. PCT/GB2015/052938, filed on Oct. 8, 2015.

(60) Provisional application No. 62/061,248, filed on Oct. 8, 2014.

(30) Foreign Application Priority Data

Oct. 8, 2014 (GB) ..................................... 1417803

(51) Int. Cl.
| | |
|---|---|
| *A61K 35/17* | (2015.01) |
| *A61K 48/00* | (2006.01) |
| *C07K 14/705* | (2006.01) |
| *C07K 14/725* | (2006.01) |
| *C07K 14/74* | (2006.01) |
| *C07K 14/47* | (2006.01) |
| *C07K 14/62* | (2006.01) |
| *C12N 5/0783* | (2010.01) |
| *A61K 38/00* | (2006.01) |

(52) U.S. Cl.
CPC ........ *C07K 14/70503* (2013.01); *A61K 35/17* (2013.01); *C07K 14/4748* (2013.01); *C07K 14/62* (2013.01); *C07K 14/7051* (2013.01); *C07K 14/70539* (2013.01); *C12N 5/0638* (2013.01); *A61K 38/00* (2013.01); *C12N 2510/00* (2013.01)

(58) Field of Classification Search
None
See application file for complete search history.

(56) References Cited

U.S. PATENT DOCUMENTS

2019/0225692 A1* 7/2019 Sissons ................ C07K 16/084

FOREIGN PATENT DOCUMENTS

| CN | 103097407 | | 5/2013 |
|---|---|---|---|
| GB | WO 06/129085 | * | 12/2006 |
| JP | 2007032255 | | 8/2007 |
| JP | 2013535199 | | 12/2013 |
| WO | WO 2011/062562 A1 | | 5/2011 |
| WO | 2012013913 | | 2/2012 |
| WO | WO 2012/038055 A1 | | 3/2012 |
| WO | 2012/091563 A1 | | 7/2012 |
| WO | 2013039889 | | 3/2013 |
| WO | WO 2013/057586 A1 | | 4/2013 |
| WO | WO 2014/036562 A2 | | 3/2014 |
| WO | 2014118236 | | 8/2014 |

OTHER PUBLICATIONS

Dutoit et al., Cancer Research, 2001, 61: 5850-5856.*
Zhong et al., Proc. Natl. Acad. Sci. USA, 2013, 110: 6973-6978.*
Morgan et al., Science, 2006, 314: 126-129.*
Schmid et al., J. Immunol., 2010, 184: 4936-4946.*
Zhao et al., J. Immunol., 2007, 179: 5845-5854.*
Card et al., Cancer Immunol. Immunother., 2004, 53: 345-357.*
Fishman et al., J. Clin. Oncol., Feb. 2013, 31, Abstract 271.*
Border et al., Oncoimmunology, 2019, 8: 1-12.*
Hoppes et al., J. Immunol., 2014, 193: 4803-4813.*
Sequence alignment_4, 2020.*
Sequence alignment_17, 2020.*
C. Linnemann, et al., High-throughput Identification of Antigen-Specific TGRs by TCR Gene Capture; Nature Medicine (Nov. 2013) vol. 19, No. 11, p. 1534-1541.
Eiji Kobayashi, et al., A New Cloning and Expression System Yields and Validates TCRs from Blood Lymphocytes of Patients with Cancer Within 10 Days, Nature Medicine (Nov. 2013) vol. 19, No. 1, p. 1542-1546.
Tatsuhiko Ozawa, et al., Comprehensive Analysis of the Functional TCR Repertoire at the Single-Cell Level, Biochemical and Biophysical Research Communications (2008) 367:820-825.
Valerie Dutoit, et al., Dissecting TCR-MHC/Peptide Complex Interactions with A2/Peptide Multimers Incorporationg Tumor Antigen Peptide Variants: Crucial Role of Interaction Kinetics on Functional Outcomes, Eur. J. Immunol. (2002) 32:3285-3293.
Michael Demetriou, et al., Negative Regulation of T-Cell Activation and Autoimmunity by Mgat5-N-Glycosylation, Nature (2001) vol. 409, No. 6821, p. 733-739.
James W. Dennis, et al., Adaptive Regulation at the Cell Surface by N-Glycosylation, Traffic (2009) 10:1569-1578.
Phillip D. Holler, et al., Quantitative Analysis of the Contribution of TCR/pepMHC Affinity and CD8 to T Cell Activation, Immunity (Feb. 2003) vol. 18, p. 255-284.

(Continued)

*Primary Examiner* — Ileana Popa
(74) *Attorney, Agent, or Firm* — Duane Morris LLP; Thomas J. Kowalski; Deborah L. Lu

(57) ABSTRACT

The present invention relates to T cell receptors (TCRs) which bind the HLA-A*02 restricted peptide GLYDG-MEHL (SEQ ID NO: 1) derived from the MAGE-A10 protein. The TCRs of the invention demonstrate excellent specificity profiles for this MAGE epitope. Also provided are nucleic acids encoding the TCRs, cells engineered to present the TCRs, cells harbouring expression vectors encoding the TCRs and pharmaceutical compositions comprising the TCRs, nucleic acids or cells of the invention.

17 Claims, 9 Drawing Sheets

Specification includes a Sequence Listing.

(56) References Cited

OTHER PUBLICATIONS

Translation Of Abstract: A. S. Ivanov, The Study of Intermolecutar Interactions Using Optical Biosensors Operating on the Effect of Surface Plasmon Resonance, Institute of Biomedical Chemistry of the Russian Academy of Medical Sciences, Sep. 24, 2012.
Andrew A. Pakula, et al., Genetic Analysis of Protein Stability and Function, Annu. Rev. Genet. (1989) 23:289-310.
Office Action issued in corresponding Russian Application No. RU2017115932, dated Apr. 4, 2019.
Huang, et al., Cytolytic T Lymphocytes Recognize an Antigen Encoded by MAGE-A10 on a Human Melanoma, The Journal of Immunology (Jun. 1, 1999) vol. 162, No. 11, p. 6849-6854.
Straetemans, et al., TCR Gene Transfer: MAGE-C2/HLA-A2 and MAGE-A3/HLA-DP4Epitopes as Melanoma-Specific Immune Targets, Clinical and Development Immunology (2012) Article ID 586314. DOI: https://doi.org/10.1155/2012/596314.
Official Action dated Oct. 4, 2020 in co-pending Brazilian Application No. 112017007202-5.
A Hiasa, et al., Long-term phenotypic, functional and genetic stability of cancer-specific T-cell receptor (TCR) ab genes transduced to CD8+ T cells, Gene Therapy (2008) vol. 15, p. 695-699.
English translation of Office Action dated Jun. 8, 2021, in corresponding Chinese Patent Application No. 2020-070831.
Written Opinion dated May 21, 2021, in corresponding Singapore Patent Application No. 11201701983W.
Hinrich Abken, et al., Antigen-specific T-cell activation independently of the MHC; chimeric antigen receptor-redirected T cells; Review Article: Frontiers in Immunology (Nov. 2013) vol. 4, Article 371, p. 1-7.
John S Bridgeman, et al., The Optimal Antigen Response of Chimeric Antigen Receptors Harboring the CD3 Z Transmembrane Domain is Dependent upon Incorporation of the Receptor info the Endogenous TCR/CD3 Complex, The Journal of Immunology (2010) 194:6938-6949.
Shaun-Paul Cordoba, et al., The large ectodomains of CD45 and CD148 regulate their segregation from and inhibition of ligated T-cell receptor, Blood (May 23, 2013) vol. 121, No. 21, p. 4295-4302.
Mshui Lian, et al.. Expressions of MAGE-A10 and MAGE-A11 in breast cancers and their prognostic significance: a retrospective clinical study, J Cancer Res. Clin Oncol. (2012) 138:519-527.
Official Action dated Aug. 24, 2021. in copending application Russian Application No. 2017115932.
Written Opinion dated Sep. 2, 2019, in corresponding Singapore Application No. 11201701983W.

\* cited by examiner

Figure 1a

Parental MAGE-A10 alpha chain extracellular amino acid sequence (SEQ ID No:2)

```
QKEVEQNSGP LSVPEGAIAS LNCTYSDRGS QSFFWYRQYS GKSPELIMSI  50
YSNGDKEDGR FTAQLNKASQ YVSLLIRDSQ PSDSATYLCA VRGTGRRALT 100
FGSGTRLQVQ PNIQNPDPAV YQLRDSKSSD KSVCLFTDFD SQTNVSQSKD 150
SDVYITDKTV LDMRSMDFKS NSAVAWSNKS DFACANAFNN SIIPEDTFFP 200
SPESS 205
```

Figure 1b

Parental MAGE-A10 TCR beta chain extracellular amino acid sequence (SEQ ID NO:3)

```
NAGVTQTPKF RVLKTGQSMT LLCAQDMNHE YMYWYRQDPG MGLRLIHYSV  50
GEGTTAKGEV PDGYNVSRLK KQNFLLGLES AAPSQTSVYF CASSFTDTQY 100
FGPGTRLTVL EDLKNVFPPE VAVFEPSEAE ISHTQKATLV CLATGFYPDH 150
VELSWWVNGK EVHSGVSTDP QPLKEQPALN DSRYCLSSRL RVSATFWQNP 200
RNHFRCQVQF YGLSENDEWT QDRAKPVTQI VSAEAWGRAD 240
```

Figure 2a

Reference TCR alpha chain – parental MAGE-A10 alpha chain extracellular amino acid sequence but with cysteine (underlined) substituted for T159 (i.e.T48 of the TRAC constant region) (SEQ ID No:4)

```
QKEVEQNSGP  LSVPEGAIAS  LNCTYSDRGS  QSFFWYRQYS  GKSPELIMSI   50
YSNGDKEDGR  FTAQLNKASQ  YVSLLIRDSQ  PSDSATYLCA  VRGTGRRALT  100
FGSGTRLQVQ  PNIQNPDPAV  YQLRDSKSSD  KSVCLFTDFD  SQTNVSQSKD  150
SDVYITDKCV  LDMRSMDFKS  NSAVAWSNKS  DFACANAFNN  SIIPEDTFFP  200
SPESS  206
```

Figure 2b

Reference TCR beta chain – parental beta chain extracellular amino acid sequence but with cysteine substituted for S167 (i.e. S57 of the TRBC2 constant region) and with A185 substituted for C185 and with D199 substituted for N199. All substitutions are underlined.
(SEQ ID No:5).

```
NAGVTQTPKF  RVLKTGQSMT  LLCAQDMNHE  YMYWYRQDPG  MGLRLIHYSV   50
GEGTTAKGEV  PDGYNVSRLK  KQNFLLGLES  AAPSQTSVYF  CASSFTDTQY  100
FGPGTRLTVL  EDLKNVFPPE  VAVFEPSEAE  ISHTQKATLV  CLATGFYPDH  150
VELSWWVNGK  EVHSGVCTDP  QPLKEQPALN  DSRYALSSRL  RVSATFWQDP  200
RNHFRCQVQF  YGLSENDEWT  QDRAKPVTQI  VSAEAWGRAD  240
```

Figure 3

Alpha chain amino acid sequences. CDRs are underlined and sequence changes from the parental alpha chain are highlighted SEQ ID No: 6 (alpha chain has single mutation encoding Gln→Ala at position 5 of alpha CDR1)

```
QKEVEQNSGP LSVPEGAIAS LNCTYSDRGS ASFFWYRQYS GKSPELIMSI  50
YSNGDKEDGR FTAQLNKASQ YVSLLIRDSQ PSDSATYLCA VRGTGRRALT 100
FGSGTRLQVQ PNIQNPDPAV YQLRDSKSSD KSVCLFTDFD SQTNVSQSKD 150
SDVYITDKTV LDMRSMDFKS NSAVAWSNKS DFACANAFNN SIIPEDTFFP 200
SPESS 206
```

SEQ ID No: 7 (alpha chain has single mutation encoding Gln→ Ser at position 5 of alpha CDR1)

```
QKEVEQNSGP LSVPEGAIAS LNCTYSDRGS SSFFWYRQYS GKSPELIMSI  50
YSNGDKEDGR FTAQLNKASQ YVSLLIRDSQ PSDSATYLCA VRGTGRRALT 100
FGSGTRLQVQ PNIQNPDPAV YQLRDSKSSD KSVCLFTDFD SQTNVSQSKD 150
SDVYITDKTV LDMRSMDFKS NSAVAWSNKS DFACANAFNN SIIPEDTFFP 200
SPESS 206
```

Figure 4

Beta chain amino acid sequences. CDRs are underlined and sequence changes from the parental alpha chain are highlighted SEQ ID No: 8 (beta chain has single mutation encoding Gly→Ser at position 3 of beta CDR2)

```
NAGVTQTPKF RVLKTGQSMT LLCAQDMNHE YMYWYRQDPG MGLRLIHYSV  50
SEGTTAKGEV PDGYNVSRLK KQNFLLGLES AAPSQTSVYF CASSFTDTQY 100
FGPGTRLTVL EDLKNVFPPE VAVFEPSEAE ISHTQKATLV CLATGFYPDH 150
VELSWWVNGK EVHSGVSTDP QPLKEQPALN DSRYCLSSRL RVSATFWQNP 200
RNHFRCQVQF YGLSENDEWT QDRAKPVTQI VSAEAWGRAD          240
```

SEQ ID No: 9 (beta chain has single mutation encoding Gly->Ala at position 3 of beta CDR2)

```
NAGVTQTPKF RVLKTGQSMT LLCAQDMNHE YMYWYRQDPG MGLRLIHYSV  50
AEGTTAKGEV PDGYNVSRLK KQNFLLGLES AAPSQTSVYF CASSFTDTQY 100
FGPGTRLTVL EDLKNVFPPE VAVFEPSEAE ISHTQKATLV CLATGFYPDH 150
VELSWWVNGK EVHSGVSTDP QPLKEQPALN DSRYCLSSRL RVSATFWQNP 200
RNHFRCQVQF YGLSENDEWT QDRAKPVTQI VSAEAWGRAD          240
```

SEQ ID No: 10 (beta chain has single mutation encoding Gly→Phe at position 3 of beta CDR2)

```
NAGVTQTPKF RVLKTGQSMT LLCAQDMNHE YMYWYRQDPG MGLRLIHYSV  50
FEGTTAKGEV PDGYNVSRLK KQNFLLGLES AAPSQTSVYF CASSFTDTQY 100
FGPGTRLTVL EDLKNVFPPE VAVFEPSEAE ISHTQKATLV CLATGFYPDH 150
VELSWWVNGK EVHSGVSTDP QPLKEQPALN DSRYCLSSRL RVSATFWQNP 200
RNHFRCQVQF YGLSENDEWT QDRAKPVTQI VSAEAWGRAD          240
```

SEQ ID No. 11 (beta chain has single mutation encoding Glu→Asp at position 4 of beta CDR1)

```
NAGVTQTPKF RVLKTGQSMT LLCAQDMNHD YMYWYRQDPG MGLRLIHYSV  50
GEGTTAKGEV PDGYNVSRLK KQNFLLGLES AAPSQTSVYF CASSFTDTQY 100
FGPGTRLTVL EDLKNVFPPE VAVFEPSEAE ISHTQKATLV CLATGFYPDH 150
VELSWWVNGK EVHSGVSTDP QPLKEQPALN DSRYCLSSRL RVSATFWQNP 200
RNHFRCQVQF YGLSENDEWT QDRAKPVTQI VSAEAWGRAD          240
```

Figure 5

Alpha chain amino acid sequences of the soluble TCRs. CDRs are underlined and sequence changes from the reference alpha chain are highlighted SEQ ID No: 12 (alpha chain has single mutation encoding Gln→Ala at position 5 of alpha CDR1)

```
QKEVEQNSGP LSVPEGAIAS LNCTYSDRGS ASFFWYRQYS GKSPELIMSI  50
YSNGDKEDGR FTAQLNKASQ YVSLLIRDSQ PSDSATYLCA VRGTGRRALT 100
FGSGTRLQVQ PNIQNPDPAV YQLRDSKSSD KSVCLFTDFD SQTNVSQSKD 150
SDVYITDKCV LDMRSMDFKS NSAVAWSNKS DFACANAFNN SIIPEDTFFP 200
SPESS 206
```

SEQ ID No: 13 (alpha chain has single mutation encoding Gln→Ser at position 5 of alpha CDR1)

```
QKEVEQNSGP LSVPEGAIAS LNCTYSDRGS SSFFWYRQYS GKSPELIMSI  50
YSNGDKEDGR FTAQLNKASQ YVSLLIRDSQ PSDSATYLCA VRGTGRRALT 100
FGSGTRLQVQ PNIQNPDPAV YQLRDSKSSD KSVCLFTDFD SQTNVSQSKD 150
SDVYITDKCV LDMRSMDFKS NSAVAWSNKS DFACANAFNN SIIPEDTFFP 200
SPESS 206
```

Figure 6

Beta chain amino acid sequences of the soluble TCRs. CDRs are underlined and sequence changes from the reference beta chain are highlighted.

SEQ ID No: 14 (beta chain has single mutation encoding Gly→Ser at position 3 of beta CDR2)

```
NAGVTQTPKF RVLKTGQSMT LLCAQDMNHE YMYWYRQDPG MGLRLIHYSV  50
SEGTTAKGEV PDGYNVSRLK KQNFLLGLES AAPSQTSVYF CASSFTDTQY 100
FGPGTRLTVL EDLKNVFPPE VAVFEPSEAE ISHTQKATLV CLATGFYPDH 150
VELSWWVNGK EVHSGVCTDP QPLKEQPALN DSRYCLSSRL RVSATFWQNP 200
RNHFRCQVQF YGLSENDEWT QDRAKPVTQI VSAEAWGRAD           240
```

SEQ ID No: 15 (beta chain has single mutation encoding Gly→Ala at position 3 of beta CDR2)

```
NAGVTQTPKF RVLKTGQSMT LLCAQDMNHE YMYWYRQDPG MGLRLIHYSV  50
AEGTTAKGEV PDGYNVSRLK KQNFLLGLES AAPSQTSVYF CASSFTDTQY 100
FGPGTRLTVL EDLKNVFPPE VAVFEPSEAE ISHTQKATLV CLATGFYPDH 150
VELSWWVNGK EVHSGVCTDP QPLKEQPALN DSRYALSSRL RVSATFWQDP 200
RNHFRCQVQF YGLSENDEWT QDRAKPVTQI VSAEAWGRAD           240
```

SEQ ID No: 16 (beta chain has single mutation encoding Gly→Phe at position 3 of beta CDR2)

```
NAGVTQTPKF RVLKTGQSMT LLCAQDMNHE YMYWYRQDPG MGLRLIHYSV  50
FEGTTAKGEV PDGYNVSRLK KQNFLLGLES AAPSQTSVYF CASSFTDTQY 100
FGPGTRLTVL EDLKNVFPPE VAVFEPSEAE ISHTQKATLV CLATGFYPDH 150
VELSWWVNGK EVHSGVCTDP QPLKEQPALN DSRYALSSRL RVSATFWQDP 200
RNHFRCQVQF YGLSENDEWT QDRAKPVTQI VSAEAWGRAD           240
```

SEQ ID No. 17 (beta chain has single mutation encoding Glu→Asp at position 4 of beta CDR1)

```
NAGVTQTPKF RVLKTGQSMT LLCAQDMNHD YMYWYRQDPG MGLRLIHYSV  50
GEGTTAKGEV PDGYNVSRLK KQNFLLGLES AAPSQTSVYF CASSFTDTQY 100
FGPGTRLTVL EDLKNVFPPE VAVFEPSEAE ISHTQKATLV CLATGFYPDH 150
VELSWWVNGK EVHSGVCTDP QPLKEQPALN DSRYALSSRL RVSATFWQNP 200
RNHFRCQVQF YGLSENDEWT QDRAKPVTQI VSAEAWGRAD           240
```

Figure 7

DNA sequence for the parental MAGE A10 TCR gene (alpha chain-2A-beta chain construct with the Porcine teschovirus-1 2A sequence)

SEQ ID No: 18 gctagccgccaccatgatgaagtccctgcgggtgctgctggtcatcctgtggctgcagctgtcctgggtctggtcccagcaga
aagaggtggagcagaacagcggccctctgagcgtgcccgagggcgctatcgccagcctgaactgcacctacagcgaca
gaggcagccagagcttcttctggtacagacagtacagcggcaagagccccgagctgatcatgagcatctacagcaacggc
gacaaagaggacggccggttcaccgcccagctgaacaaggccagccagtacgtgtccctgctgatccgggacagccagc
ccagcgacagcgccacctacctgtgcgccgtgagaggcacaggcagaagggccctgacatttggcagcggcaccagact
gcaggtgcagcccaatattcagaaccccgaccccgccgtgtaccagctgcgggacagcaagagcagcgacaagagcgt
gtgcctgttcaccgacttcgacagccagaccaacgtgtcccagagcaaggacagcgacgtgtacatcaccgacaagaccg
tgctggacatgcggagcatggacttcaagagcaacagcgccgtggcctggtccaacaagagcgacttcgcctgcgccaac
gccttcaacaacagcatcatccccgaggacaccttttcccagccccgagagcagctgcgacgtcaaactggtggagaag
tccttcgagacagacaccaacctgaacttccagaacctgagcgtgatcggcttcagaatcctgctgctgaaggtggccggctt
caatctgctgatgaccctgcggctgtggagcagcggcagccgggccaagagaagcggatccggcgccaccaacttcagc
ctgctgaagcaggccggcgacgtggaggaaaaccctggccctaggatgtctctgggcctgctgtgctgtggcgtgttctccct
gctgtgggccggacctgtgaatgccggcgtgacccagacccccaagttccgggtgctgaaaaccggccagagcatgaca
ctgctgtgcgcccaggacatgaaccacgagtacatgtattggtacagacaggaccccggcatgggcctgcggctgatccac
tattctgtgggcgagggcaccaccgccaagggcgaagtgcctgatggctacaacgtgtcccggctgaagaagcagaacttc
ctgctgggcctggaaagcgccgctcctagccagaccagcgtgtacttctgcgccagcagcttcaccgacacccagtacttcg
gccctggcaccagactgaccgtgctggaggacctgaagaacgtgttccccccagaggtggccgtgttcgagccctctgagg
ccgagatcagccacacccagaaagccaccctggtctgcctggccaccggcttctaccccgaccacgtggaactgtcttggtg
ggtgaacggcaaagaggtgcacagcggcgtcagcaccgaccctcagcccctgaaagagcagcccgccctgaacgaca
gccggtactgcctgagcagcagactgcgggtgtccgccaccttctggcagaaccccggaaccacttcagatgccaggtgc
agttctacggcctgagcgagaacgacgagtggacccaggaccgggccaagcctgtgacccagatcgtgtctgccgaagc
atgggggcgcgccgattgcggcttcacaagcgagagctaccagcagggcgtgctgagcgccaccatcctgtacgagatcc
tgctgggcaaggccaccctgtacgccgtgctggtgtccgctctggtgctgatggccatggtgaaacggaaggacagccggg
gctaataagtcgac

Figure 8

Amino acid sequence of the parental MAGE A10 TCR for T-cell transduction produced from the DNA sequence of Figure 7. The Porcine teschovirus-1 2A sequence is bold and underlined.

SEQ ID NO: 19

```
MMKSLRVLLV ILWLQLSWVW SQQKEVEQNS GPLSVPEGAI ASLNCTYSDR   50
GSQSFFWYRQ YSGKSPELIM SIYSNGDKED GRFTAQLNKA SQYVSLLIRD  100
SQPSDSATYL CAVRGTGRRA LTFGSGTRLQ VQPNIQNPDP AVYQLRDSKS  150
SDKSVCLFTD FDSQTNVSQS KDSDVYITDK TVLDMRSMDF KSNSAVAWSN  200
KSDFACANAF NNSIIPEDTF FPSPESSCDV KLVEKSFETD TNLNFQNLSV  250
IGFRILLLKV AGFNLLMTLR LWSSGSRAKR SGSGATNFSL LKQAGDVEEN  300
PGPRMSLGLL CCGVFSLLWA GPVNAGVTQT PKFRVLKTGQ SMTLLCAQDM  350
NHEYMYWYRQ DPGMGLRLIH YSVGEGTTAK GEVPDGYNVS RLKKQNFLLG  400
LESAAPSQTS VYFCASSFTD TQYFGPGTRL TVLEDLKNVF PPEVAVFEPS  450
EAEISHTQKA TLVCLATGFY PDHVELSWWV NGKEVHSGVS TDPQPLKEQP  500
ALNDSRYCLS SRLRVSATFW QNPRNHFRCQ VQFYGLSEND EWTQDRAKPV  550
TQIVSAEAWG RADCGFTSES YQQGVLSATI LYEILLGKAT LYAVLVSALV  600
LMAMVKRKDS RG   612
```

Activation of MAGE-A10 TCR engineered T-cells (IFNγ production)

SEQUENCE LISTING

```
<160> NUMBER OF SEQ ID NOS: 19

<210> SEQ ID NO 1
<211> LENGTH: 9
<212> TYPE: PRT
<213> ORGANISM: Homo sapiens

<400> SEQUENCE: 1

Gly Leu Tyr Asp Gly Met Glu His Leu
1               5

<210> SEQ ID NO 2
<211> LENGTH: 205
<212> TYPE: PRT
<213> ORGANISM: Homo sapiens

<400> SEQUENCE: 2

Gln Lys Glu Val Glu Gln Asn Ser Gly Pro Leu Ser Val Pro Glu Gly
1               5                   10                  15
```

-continued

```
Ala Ile Ala Ser Leu Asn Cys Thr Tyr Ser Asp Arg Gly Gln Ser
             20                  25                  30

Phe Phe Trp Tyr Arg Gln Tyr Ser Gly Lys Ser Pro Glu Leu Ile Met
         35                  40                  45

Ser Ile Tyr Ser Asn Gly Asp Lys Glu Asp Gly Arg Phe Thr Ala Gln
     50                  55                  60

Leu Asn Lys Ala Ser Gln Tyr Val Ser Leu Leu Ile Arg Asp Ser Gln
 65                  70                  75                  80

Pro Ser Asp Ser Ala Thr Tyr Leu Cys Ala Val Arg Gly Thr Gly Arg
                 85                  90                  95

Arg Ala Leu Thr Phe Gly Ser Gly Thr Arg Leu Gln Val Gln Pro Asn
                100                 105                 110

Ile Gln Asn Pro Asp Pro Ala Val Tyr Gln Leu Arg Asp Ser Lys Ser
            115                 120                 125

Ser Asp Lys Ser Val Cys Leu Phe Thr Asp Phe Asp Ser Gln Thr Asn
        130                 135                 140

Val Ser Gln Ser Lys Asp Ser Asp Val Tyr Ile Thr Asp Lys Thr Val
145                 150                 155                 160

Leu Asp Met Arg Ser Met Asp Phe Lys Ser Asn Ser Ala Val Ala Trp
                165                 170                 175

Ser Asn Lys Ser Asp Phe Ala Cys Ala Asn Ala Phe Asn Asn Ser Ile
            180                 185                 190

Ile Pro Glu Asp Thr Phe Phe Pro Ser Pro Glu Ser Ser
        195                 200                 205

<210> SEQ ID NO 3
<211> LENGTH: 240
<212> TYPE: PRT
<213> ORGANISM: Homo sapiens

<400> SEQUENCE: 3

Asn Ala Gly Val Thr Gln Thr Pro Lys Phe Arg Val Leu Lys Thr Gly
 1               5                  10                  15

Gln Ser Met Thr Leu Leu Cys Ala Gln Asp Met Asn His Glu Tyr Met
             20                  25                  30

Tyr Trp Tyr Arg Gln Asp Pro Gly Met Gly Leu Arg Leu Ile His Tyr
         35                  40                  45

Ser Val Gly Glu Gly Thr Thr Ala Lys Gly Glu Val Pro Asp Gly Tyr
     50                  55                  60

Asn Val Ser Arg Leu Lys Lys Gln Asn Phe Leu Leu Gly Leu Glu Ser
 65                  70                  75                  80

Ala Ala Pro Ser Gln Thr Ser Val Tyr Phe Cys Ala Ser Ser Phe Thr
                 85                  90                  95

Asp Thr Gln Tyr Phe Gly Pro Gly Thr Arg Leu Thr Val Leu Glu Asp
                100                 105                 110

Leu Lys Asn Val Phe Pro Pro Glu Val Ala Val Phe Glu Pro Ser Glu
            115                 120                 125

Ala Glu Ile Ser His Thr Gln Lys Ala Thr Leu Val Cys Leu Ala Thr
        130                 135                 140

Gly Phe Tyr Pro Asp His Val Glu Leu Ser Trp Trp Val Asn Gly Lys
145                 150                 155                 160

Glu Val His Ser Gly Val Ser Thr Asp Pro Gln Pro Leu Lys Glu Gln
                165                 170                 175

Pro Ala Leu Asn Asp Ser Arg Tyr Cys Leu Ser Ser Arg Leu Arg Val
            180                 185                 190
```

```
Ser Ala Thr Phe Trp Gln Asn Pro Arg Asn His Phe Arg Cys Gln Val
        195                 200                 205

Gln Phe Tyr Gly Leu Ser Glu Asn Asp Glu Trp Thr Gln Asp Arg Ala
        210                 215                 220

Lys Pro Val Thr Gln Ile Val Ser Ala Glu Ala Trp Gly Arg Ala Asp
225                 230                 235                 240

<210> SEQ ID NO 4
<211> LENGTH: 205
<212> TYPE: PRT
<213> ORGANISM: Artificial Sequence
<220> FEATURE:
<223> OTHER INFORMATION: Reference TCR alpha chain

<400> SEQUENCE: 4

Gln Lys Glu Val Glu Gln Asn Ser Gly Pro Leu Ser Val Pro Glu Gly
1               5                   10                  15

Ala Ile Ala Ser Leu Asn Cys Thr Tyr Ser Asp Arg Gly Ser Gln Ser
            20                  25                  30

Phe Phe Trp Tyr Arg Gln Tyr Ser Gly Lys Ser Pro Glu Leu Ile Met
        35                  40                  45

Ser Ile Tyr Ser Asn Gly Asp Lys Glu Asp Gly Arg Phe Thr Ala Gln
    50                  55                  60

Leu Asn Lys Ala Ser Gln Tyr Val Ser Leu Leu Ile Arg Asp Ser Gln
65                  70                  75                  80

Pro Ser Asp Ser Ala Thr Tyr Leu Cys Ala Val Arg Gly Thr Gly Arg
                85                  90                  95

Arg Ala Leu Thr Phe Gly Ser Gly Thr Arg Leu Gln Val Gln Pro Asn
            100                 105                 110

Ile Gln Asn Pro Asp Pro Ala Val Tyr Gln Leu Arg Asp Ser Lys Ser
        115                 120                 125

Ser Asp Lys Ser Val Cys Leu Phe Thr Asp Phe Asp Ser Gln Thr Asn
    130                 135                 140

Val Ser Gln Ser Lys Asp Ser Asp Val Tyr Ile Thr Asp Lys Cys Val
145                 150                 155                 160

Leu Asp Met Arg Ser Met Asp Phe Lys Ser Asn Ser Ala Val Ala Trp
                165                 170                 175

Ser Asn Lys Ser Asp Phe Ala Cys Ala Asn Ala Phe Asn Asn Ser Ile
            180                 185                 190

Ile Pro Glu Asp Thr Phe Phe Pro Ser Pro Glu Ser Ser
        195                 200                 205

<210> SEQ ID NO 5
<211> LENGTH: 240
<212> TYPE: PRT
<213> ORGANISM: Artificial Sequence
<220> FEATURE:
<223> OTHER INFORMATION: Reference TCR beta chain

<400> SEQUENCE: 5

Asn Ala Gly Val Thr Gln Thr Pro Lys Phe Arg Val Leu Lys Thr Gly
1               5                   10                  15

Gln Ser Met Thr Leu Leu Cys Ala Gln Asp Met Asn His Glu Tyr Met
            20                  25                  30

Tyr Trp Tyr Arg Gln Asp Pro Gly Met Gly Leu Arg Leu Ile His Tyr
        35                  40                  45

Ser Val Gly Glu Gly Thr Thr Ala Lys Gly Glu Val Pro Asp Gly Tyr
```

```
            50                  55                  60
Asn Val Ser Arg Leu Lys Lys Gln Asn Phe Leu Leu Gly Leu Glu Ser
 65                  70                  75                  80

Ala Ala Pro Ser Gln Thr Ser Val Tyr Phe Cys Ala Ser Ser Phe Thr
                 85                  90                  95

Asp Thr Gln Tyr Phe Gly Pro Gly Thr Arg Leu Thr Val Leu Glu Asp
                100                 105                 110

Leu Lys Asn Val Phe Pro Pro Glu Val Ala Val Phe Glu Pro Ser Glu
                115                 120                 125

Ala Glu Ile Ser His Thr Gln Lys Ala Thr Leu Val Cys Leu Ala Thr
                130                 135                 140

Gly Phe Tyr Pro Asp His Val Glu Leu Ser Trp Trp Val Asn Gly Lys
145                 150                 155                 160

Glu Val His Ser Gly Val Cys Thr Asp Pro Gln Pro Leu Lys Glu Gln
                165                 170                 175

Pro Ala Leu Asn Asp Ser Arg Tyr Ala Leu Ser Ser Arg Leu Arg Val
                180                 185                 190

Ser Ala Thr Phe Trp Gln Asp Pro Arg Asn His Phe Arg Cys Gln Val
                195                 200                 205

Gln Phe Tyr Gly Leu Ser Glu Asn Asp Glu Trp Thr Gln Asp Arg Ala
                210                 215                 220

Lys Pro Val Thr Gln Ile Val Ser Ala Glu Ala Trp Gly Arg Ala Asp
225                 230                 235                 240

<210> SEQ ID NO 6
<211> LENGTH: 205
<212> TYPE: PRT
<213> ORGANISM: Artificial Sequence
<220> FEATURE:
<223> OTHER INFORMATION: Alpha chain amino acid sequence

<400> SEQUENCE: 6

Gln Lys Glu Val Glu Gln Asn Ser Gly Pro Leu Ser Val Pro Glu Gly
 1               5                  10                  15

Ala Ile Ala Ser Leu Asn Cys Thr Tyr Ser Asp Arg Gly Ser Ala Ser
                 20                  25                  30

Phe Phe Trp Tyr Arg Gln Tyr Ser Gly Lys Ser Pro Glu Leu Ile Met
                 35                  40                  45

Ser Ile Tyr Ser Asn Gly Asp Lys Glu Asp Gly Arg Phe Thr Ala Gln
 50                  55                  60

Leu Asn Lys Ala Ser Gln Tyr Val Ser Leu Leu Ile Arg Asp Ser Gln
 65                  70                  75                  80

Pro Ser Asp Ser Ala Thr Tyr Leu Cys Ala Val Arg Gly Thr Gly Arg
                 85                  90                  95

Arg Ala Leu Thr Phe Gly Ser Gly Thr Arg Leu Gln Val Gln Pro Asn
                100                 105                 110

Ile Gln Asn Pro Asp Pro Ala Val Tyr Gln Leu Arg Asp Ser Lys Ser
                115                 120                 125

Ser Asp Lys Ser Val Cys Leu Phe Thr Asp Phe Asp Ser Gln Thr Asn
                130                 135                 140

Val Ser Gln Ser Lys Asp Ser Asp Val Tyr Ile Thr Asp Lys Thr Val
145                 150                 155                 160

Leu Asp Met Arg Ser Met Asp Phe Lys Ser Asn Ser Ala Val Ala Trp
                165                 170                 175

Ser Asn Lys Ser Asp Phe Ala Cys Ala Asn Ala Phe Asn Asn Ser Ile
```

```
            180                 185                 190

Ile Pro Glu Asp Thr Phe Phe Pro Ser Pro Glu Ser Ser
            195                 200                 205

<210> SEQ ID NO 7
<211> LENGTH: 205
<212> TYPE: PRT
<213> ORGANISM: Artificial Sequence
<220> FEATURE:
<223> OTHER INFORMATION: Alpha chain amino acid sequence

<400> SEQUENCE: 7

Gln Lys Glu Val Glu Gln Asn Ser Gly Pro Leu Ser Val Pro Glu Gly
1               5                   10                  15

Ala Ile Ala Ser Leu Asn Cys Thr Tyr Ser Asp Arg Gly Ser Ser Ser
                20                  25                  30

Phe Phe Trp Tyr Arg Gln Tyr Ser Gly Lys Ser Pro Glu Leu Ile Met
            35                  40                  45

Ser Ile Tyr Ser Asn Gly Asp Lys Glu Asp Gly Arg Phe Thr Ala Gln
    50                  55                  60

Leu Asn Lys Ala Ser Gln Tyr Val Ser Leu Leu Ile Arg Asp Ser Gln
65                  70                  75                  80

Pro Ser Asp Ser Ala Thr Tyr Leu Cys Ala Val Arg Gly Thr Gly Arg
                85                  90                  95

Arg Ala Leu Thr Phe Gly Ser Gly Thr Arg Leu Gln Val Gln Pro Asn
            100                 105                 110

Ile Gln Asn Pro Asp Pro Ala Val Tyr Gln Leu Arg Asp Ser Lys Ser
        115                 120                 125

Ser Asp Lys Ser Val Cys Leu Phe Thr Asp Phe Asp Ser Gln Thr Asn
    130                 135                 140

Val Ser Gln Ser Lys Asp Ser Asp Val Tyr Ile Thr Asp Lys Thr Val
145                 150                 155                 160

Leu Asp Met Arg Ser Met Asp Phe Lys Ser Asn Ser Ala Val Ala Trp
                165                 170                 175

Ser Asn Lys Ser Asp Phe Ala Cys Ala Asn Ala Phe Asn Asn Ser Ile
            180                 185                 190

Ile Pro Glu Asp Thr Phe Phe Pro Ser Pro Glu Ser Ser
        195                 200                 205

<210> SEQ ID NO 8
<211> LENGTH: 240
<212> TYPE: PRT
<213> ORGANISM: Artificial Sequence
<220> FEATURE:
<223> OTHER INFORMATION: Beta chain amino acid sequence

<400> SEQUENCE: 8

Asn Ala Gly Val Thr Gln Thr Pro Lys Phe Arg Val Leu Lys Thr Gly
1               5                   10                  15

Gln Ser Met Thr Leu Leu Cys Ala Gln Asp Met Asn His Glu Tyr Met
                20                  25                  30

Tyr Trp Tyr Arg Gln Asp Pro Gly Met Gly Leu Arg Leu Ile His Tyr
            35                  40                  45

Ser Val Ser Glu Gly Thr Thr Ala Lys Gly Glu Val Pro Asp Gly Tyr
    50                  55                  60

Asn Val Ser Arg Leu Lys Lys Gln Asn Phe Leu Leu Gly Leu Glu Ser
65                  70                  75                  80
```

```
Ala Ala Pro Ser Gln Thr Ser Val Tyr Phe Cys Ala Ser Ser Phe Thr
                85                  90                  95

Asp Thr Gln Tyr Phe Gly Pro Gly Thr Arg Leu Thr Val Leu Glu Asp
            100                 105                 110

Leu Lys Asn Val Phe Pro Pro Glu Val Ala Val Phe Glu Pro Ser Glu
            115                 120                 125

Ala Glu Ile Ser His Thr Gln Lys Ala Thr Leu Val Cys Leu Ala Thr
            130                 135                 140

Gly Phe Tyr Pro Asp His Val Glu Leu Ser Trp Trp Val Asn Gly Lys
145                 150                 155                 160

Glu Val His Ser Gly Val Ser Thr Asp Pro Gln Pro Leu Lys Glu Gln
                165                 170                 175

Pro Ala Leu Asn Asp Ser Arg Tyr Cys Leu Ser Ser Arg Leu Arg Val
            180                 185                 190

Ser Ala Thr Phe Trp Gln Asn Pro Arg Asn His Phe Arg Cys Gln Val
            195                 200                 205

Gln Phe Tyr Gly Leu Ser Glu Asn Asp Glu Trp Thr Gln Asp Arg Ala
            210                 215                 220

Lys Pro Val Thr Gln Ile Val Ser Ala Glu Ala Trp Gly Arg Ala Asp
225                 230                 235                 240

<210> SEQ ID NO 9
<211> LENGTH: 240
<212> TYPE: PRT
<213> ORGANISM: Artificial Sequence
<220> FEATURE:
<223> OTHER INFORMATION: Beta chain amino acid sequence

<400> SEQUENCE: 9

Asn Ala Gly Val Thr Gln Thr Pro Lys Phe Arg Val Leu Lys Thr Gly
1               5                   10                  15

Gln Ser Met Thr Leu Cys Ala Gln Asp Met Asn His Glu Tyr Met
                20                  25                  30

Tyr Trp Tyr Arg Gln Asp Pro Gly Met Gly Leu Arg Leu Ile His Tyr
            35                  40                  45

Ser Val Ala Glu Gly Thr Thr Ala Lys Gly Glu Val Pro Asp Gly Tyr
50                  55                  60

Asn Val Ser Arg Leu Lys Lys Gln Asn Phe Leu Leu Gly Leu Glu Ser
65                  70                  75                  80

Ala Ala Pro Ser Gln Thr Ser Val Tyr Phe Cys Ala Ser Ser Phe Thr
                85                  90                  95

Asp Thr Gln Tyr Phe Gly Pro Gly Thr Arg Leu Thr Val Leu Glu Asp
            100                 105                 110

Leu Lys Asn Val Phe Pro Pro Glu Val Ala Val Phe Glu Pro Ser Glu
            115                 120                 125

Ala Glu Ile Ser His Thr Gln Lys Ala Thr Leu Val Cys Leu Ala Thr
            130                 135                 140

Gly Phe Tyr Pro Asp His Val Glu Leu Ser Trp Trp Val Asn Gly Lys
145                 150                 155                 160

Glu Val His Ser Gly Val Ser Thr Asp Pro Gln Pro Leu Lys Glu Gln
                165                 170                 175

Pro Ala Leu Asn Asp Ser Arg Tyr Cys Leu Ser Ser Arg Leu Arg Val
            180                 185                 190

Ser Ala Thr Phe Trp Gln Asn Pro Arg Asn His Phe Arg Cys Gln Val
            195                 200                 205
```

-continued

Gln Phe Tyr Gly Leu Ser Glu Asn Asp Glu Trp Thr Gln Asp Arg Ala
210                 215                 220

Lys Pro Val Thr Gln Ile Val Ser Ala Glu Ala Trp Gly Arg Ala Asp
225                 230                 235                 240

<210> SEQ ID NO 10
<211> LENGTH: 240
<212> TYPE: PRT
<213> ORGANISM: Artificial Sequence
<220> FEATURE:
<223> OTHER INFORMATION: Beta chain amino acid sequence

<400> SEQUENCE: 10

Asn Ala Gly Val Thr Gln Thr Pro Lys Phe Arg Val Leu Lys Thr Gly
1               5                   10                  15

Gln Ser Met Thr Leu Leu Cys Ala Gln Asp Met Asn His Glu Tyr Met
                20                  25                  30

Tyr Trp Tyr Arg Gln Asp Pro Gly Met Gly Leu Arg Leu Ile His Tyr
            35                  40                  45

Ser Val Phe Glu Gly Thr Thr Ala Lys Gly Glu Val Pro Asp Gly Tyr
        50                  55                  60

Asn Val Ser Arg Leu Lys Lys Gln Asn Phe Leu Leu Gly Leu Glu Ser
65                  70                  75                  80

Ala Ala Pro Ser Gln Thr Ser Val Tyr Phe Cys Ala Ser Ser Phe Thr
                85                  90                  95

Asp Thr Gln Tyr Phe Gly Pro Gly Thr Arg Leu Thr Val Leu Glu Asp
            100                 105                 110

Leu Lys Asn Val Phe Pro Pro Glu Val Ala Val Phe Glu Pro Ser Glu
        115                 120                 125

Ala Glu Ile Ser His Thr Gln Lys Ala Thr Leu Val Cys Leu Ala Thr
130                 135                 140

Gly Phe Tyr Pro Asp His Val Glu Leu Ser Trp Trp Val Asn Gly Lys
145                 150                 155                 160

Glu Val His Ser Gly Val Ser Thr Asp Pro Gln Pro Leu Lys Glu Gln
                165                 170                 175

Pro Ala Leu Asn Asp Ser Arg Tyr Cys Leu Ser Ser Arg Leu Arg Val
            180                 185                 190

Ser Ala Thr Phe Trp Gln Asn Pro Arg Asn His Phe Arg Cys Gln Val
        195                 200                 205

Gln Phe Tyr Gly Leu Ser Glu Asn Asp Glu Trp Thr Gln Asp Arg Ala
210                 215                 220

Lys Pro Val Thr Gln Ile Val Ser Ala Glu Ala Trp Gly Arg Ala Asp
225                 230                 235                 240

<210> SEQ ID NO 11
<211> LENGTH: 240
<212> TYPE: PRT
<213> ORGANISM: Artificial Sequence
<220> FEATURE:
<223> OTHER INFORMATION: Beta chain amino acid sequence

<400> SEQUENCE: 11

Asn Ala Gly Val Thr Gln Thr Pro Lys Phe Arg Val Leu Lys Thr Gly
1               5                   10                  15

Gln Ser Met Thr Leu Leu Cys Ala Gln Asp Met Asn His Asp Tyr Met
                20                  25                  30

Tyr Trp Tyr Arg Gln Asp Pro Gly Met Gly Leu Arg Leu Ile His Tyr
            35                  40                  45

```
Ser Val Gly Glu Gly Thr Thr Ala Lys Gly Glu Val Pro Asp Gly Tyr
    50                  55                  60

Asn Val Ser Arg Leu Lys Lys Gln Asn Phe Leu Gly Leu Glu Ser
65                  70                  75                  80

Ala Ala Pro Ser Gln Thr Ser Val Tyr Phe Cys Ala Ser Ser Phe Thr
                    85                  90                  95

Asp Thr Gln Tyr Phe Gly Pro Gly Thr Arg Leu Thr Val Leu Glu Asp
                100                 105                 110

Leu Lys Asn Val Phe Pro Pro Glu Val Ala Val Phe Glu Pro Ser Glu
                115                 120                 125

Ala Glu Ile Ser His Thr Gln Lys Ala Thr Leu Val Cys Leu Ala Thr
                130                 135                 140

Gly Phe Tyr Pro Asp His Val Glu Leu Ser Trp Trp Val Asn Gly Lys
145                 150                 155                 160

Glu Val His Ser Gly Val Ser Thr Asp Pro Gln Pro Leu Lys Glu Gln
                165                 170                 175

Pro Ala Leu Asn Asp Ser Arg Tyr Cys Leu Ser Ser Arg Leu Arg Val
                180                 185                 190

Ser Ala Thr Phe Trp Gln Asn Pro Arg Asn His Phe Arg Cys Gln Val
                195                 200                 205

Gln Phe Tyr Gly Leu Ser Glu Asn Asp Glu Trp Thr Gln Asp Arg Ala
                210                 215                 220

Lys Pro Val Thr Gln Ile Val Ser Ala Glu Ala Trp Gly Arg Ala Asp
225                 230                 235                 240

<210> SEQ ID NO 12
<211> LENGTH: 205
<212> TYPE: PRT
<213> ORGANISM: Artificial Sequence
<220> FEATURE:
<223> OTHER INFORMATION: Alpha chain amino acid sequence of soluble TCR

<400> SEQUENCE: 12

Gln Lys Glu Val Glu Gln Asn Ser Gly Pro Leu Ser Val Pro Glu Gly
1               5                   10                  15

Ala Ile Ala Ser Leu Asn Cys Thr Tyr Ser Asp Arg Gly Ser Ala Ser
                20                  25                  30

Phe Phe Trp Tyr Arg Gln Tyr Ser Gly Lys Ser Pro Glu Leu Ile Met
                35                  40                  45

Ser Ile Tyr Ser Asn Gly Asp Lys Glu Asp Gly Arg Phe Thr Ala Gln
    50                  55                  60

Leu Asn Lys Ala Ser Gln Tyr Val Ser Leu Leu Ile Arg Asp Ser Gln
65                  70                  75                  80

Pro Ser Asp Ser Ala Thr Tyr Leu Cys Ala Val Arg Gly Thr Gly Arg
                85                  90                  95

Arg Ala Leu Thr Phe Gly Ser Gly Thr Arg Leu Gln Val Gln Pro Asn
                100                 105                 110

Ile Gln Asn Pro Asp Pro Ala Val Tyr Gln Leu Arg Asp Ser Lys Ser
                115                 120                 125

Ser Asp Lys Ser Val Cys Leu Phe Thr Asp Phe Asp Ser Gln Thr Asn
                130                 135                 140

Val Ser Gln Ser Lys Asp Ser Asp Val Tyr Ile Thr Asp Lys Cys Val
145                 150                 155                 160

Leu Asp Met Arg Ser Met Asp Phe Lys Ser Asn Ser Ala Val Ala Trp
                165                 170                 175
```

```
Ser Asn Lys Ser Asp Phe Ala Cys Ala Asn Ala Phe Asn Asn Ser Ile
            180                 185                 190

Ile Pro Glu Asp Thr Phe Phe Pro Ser Pro Glu Ser Ser
            195                 200                 205

<210> SEQ ID NO 13
<211> LENGTH: 205
<212> TYPE: PRT
<213> ORGANISM: Artificial Sequence
<220> FEATURE:
<223> OTHER INFORMATION: Alpha chain amino acid sequence of soluble TCR

<400> SEQUENCE: 13

Gln Lys Glu Val Glu Gln Asn Ser Gly Pro Leu Ser Val Pro Glu Gly
1               5                   10                  15

Ala Ile Ala Ser Leu Asn Cys Thr Tyr Ser Asp Arg Gly Ser Ser Ser
            20                  25                  30

Phe Phe Trp Tyr Arg Gln Tyr Ser Gly Lys Ser Pro Glu Leu Ile Met
        35                  40                  45

Ser Ile Tyr Ser Asn Gly Asp Lys Glu Asp Gly Arg Phe Thr Ala Gln
50                  55                  60

Leu Asn Lys Ala Ser Gln Tyr Val Ser Leu Leu Ile Arg Asp Ser Gln
65                  70                  75                  80

Pro Ser Asp Ser Ala Thr Tyr Leu Cys Ala Val Arg Gly Thr Gly Arg
                85                  90                  95

Arg Ala Leu Thr Phe Gly Ser Gly Thr Arg Leu Gln Val Gln Pro Asn
            100                 105                 110

Ile Gln Asn Pro Asp Pro Ala Val Tyr Gln Leu Arg Asp Ser Lys Ser
        115                 120                 125

Ser Asp Lys Ser Val Cys Leu Phe Thr Asp Phe Asp Ser Gln Thr Asn
130                 135                 140

Val Ser Gln Ser Lys Asp Ser Asp Val Tyr Ile Thr Asp Lys Cys Val
145                 150                 155                 160

Leu Asp Met Arg Ser Met Asp Phe Lys Ser Asn Ser Ala Val Ala Trp
                165                 170                 175

Ser Asn Lys Ser Asp Phe Ala Cys Ala Asn Ala Phe Asn Asn Ser Ile
            180                 185                 190

Ile Pro Glu Asp Thr Phe Phe Pro Ser Pro Glu Ser Ser
        195                 200                 205

<210> SEQ ID NO 14
<211> LENGTH: 240
<212> TYPE: PRT
<213> ORGANISM: Artificial Sequence
<220> FEATURE:
<223> OTHER INFORMATION: Beta chain amino acid sequence of soluble TCR

<400> SEQUENCE: 14

Asn Ala Gly Val Thr Gln Thr Pro Lys Phe Arg Val Leu Lys Thr Gly
1               5                   10                  15

Gln Ser Met Thr Leu Leu Cys Ala Gln Asp Met Asn His Glu Tyr Met
            20                  25                  30

Tyr Trp Tyr Arg Gln Asp Pro Gly Met Gly Leu Arg Leu Ile His Tyr
        35                  40                  45

Ser Val Ser Glu Gly Thr Thr Ala Lys Gly Glu Val Pro Asp Gly Tyr
50                  55                  60

Asn Val Ser Arg Leu Lys Lys Gln Asn Phe Leu Leu Gly Leu Glu Ser
```

```
                65                  70                  75                  80
Ala Ala Pro Ser Gln Thr Ser Val Tyr Phe Cys Ala Ser Ser Phe Thr
                    85                  90                  95

Asp Thr Gln Tyr Phe Gly Pro Gly Thr Arg Leu Thr Val Leu Glu Asp
                    100                 105                 110

Leu Lys Asn Val Phe Pro Pro Glu Val Ala Val Phe Glu Pro Ser Glu
                    115                 120                 125

Ala Glu Ile Ser His Thr Gln Lys Ala Thr Leu Val Cys Leu Ala Thr
                    130                 135                 140

Gly Phe Tyr Pro Asp His Val Glu Leu Ser Trp Trp Val Asn Gly Lys
145                 150                 155                 160

Glu Val His Ser Gly Val Cys Thr Asp Pro Gln Pro Leu Lys Glu Gln
                    165                 170                 175

Pro Ala Leu Asn Asp Ser Arg Tyr Cys Leu Ser Ser Arg Leu Arg Val
                    180                 185                 190

Ser Ala Thr Phe Trp Gln Asn Pro Arg Asn His Phe Arg Cys Gln Val
                    195                 200                 205

Gln Phe Tyr Gly Leu Ser Glu Asn Asp Glu Trp Thr Gln Asp Arg Ala
                    210                 215                 220

Lys Pro Val Thr Gln Ile Val Ser Ala Glu Ala Trp Gly Arg Ala Asp
225                 230                 235                 240

<210> SEQ ID NO 15
<211> LENGTH: 240
<212> TYPE: PRT
<213> ORGANISM: Artificial Sequence
<220> FEATURE:
<223> OTHER INFORMATION: Beta chain amino acid sequence of soluble TCR

<400> SEQUENCE: 15

Asn Ala Gly Val Thr Gln Thr Pro Lys Phe Arg Val Leu Lys Thr Gly
1               5                   10                  15

Gln Ser Met Thr Leu Leu Cys Ala Gln Asp Met Asn His Glu Tyr Met
                20                  25                  30

Tyr Trp Tyr Arg Gln Asp Pro Gly Met Gly Leu Arg Leu Ile His Tyr
                35                  40                  45

Ser Val Ala Glu Gly Thr Thr Ala Lys Gly Glu Val Pro Asp Gly Tyr
            50                  55                  60

Asn Val Ser Arg Leu Lys Lys Gln Asn Phe Leu Gly Leu Glu Ser
65                  70                  75                  80

Ala Ala Pro Ser Gln Thr Ser Val Tyr Phe Cys Ala Ser Ser Phe Thr
                    85                  90                  95

Asp Thr Gln Tyr Phe Gly Pro Gly Thr Arg Leu Thr Val Leu Glu Asp
                    100                 105                 110

Leu Lys Asn Val Phe Pro Pro Glu Val Ala Val Phe Glu Pro Ser Glu
                    115                 120                 125

Ala Glu Ile Ser His Thr Gln Lys Ala Thr Leu Val Cys Leu Ala Thr
                    130                 135                 140

Gly Phe Tyr Pro Asp His Val Glu Leu Ser Trp Trp Val Asn Gly Lys
145                 150                 155                 160

Glu Val His Ser Gly Val Cys Thr Asp Pro Gln Pro Leu Lys Glu Gln
                    165                 170                 175

Pro Ala Leu Asn Asp Ser Arg Tyr Ala Leu Ser Ser Arg Leu Arg Val
                    180                 185                 190

Ser Ala Thr Phe Trp Gln Asp Pro Arg Asn His Phe Arg Cys Gln Val
```

195                 200                 205
Gln Phe Tyr Gly Leu Ser Glu Asn Asp Glu Trp Thr Gln Asp Arg Ala
    210                 215                 220

Lys Pro Val Thr Gln Ile Val Ser Ala Glu Ala Trp Gly Arg Ala Asp
225                 230                 235                 240

<210> SEQ ID NO 16
<211> LENGTH: 240
<212> TYPE: PRT
<213> ORGANISM: Artificial Sequence
<220> FEATURE:
<223> OTHER INFORMATION: Beta chain amino acid sequence of soluble TCR

<400> SEQUENCE: 16

Asn Ala Gly Val Thr Gln Thr Pro Lys Phe Arg Val Leu Lys Thr Gly
1               5                   10                  15

Gln Ser Met Thr Leu Leu Cys Ala Gln Asp Met Asn His Glu Tyr Met
            20                  25                  30

Tyr Trp Tyr Arg Gln Asp Pro Gly Met Gly Leu Arg Leu Ile His Tyr
        35                  40                  45

Ser Val Phe Glu Gly Thr Thr Ala Lys Gly Glu Val Pro Asp Gly Tyr
    50                  55                  60

Asn Val Ser Arg Leu Lys Lys Gln Asn Phe Leu Leu Gly Leu Glu Ser
65                  70                  75                  80

Ala Ala Pro Ser Gln Thr Ser Val Tyr Phe Cys Ala Ser Ser Phe Thr
                85                  90                  95

Asp Thr Gln Tyr Phe Gly Pro Gly Thr Arg Leu Thr Val Leu Glu Asp
            100                 105                 110

Leu Lys Asn Val Phe Pro Pro Glu Val Ala Val Phe Glu Pro Ser Glu
        115                 120                 125

Ala Glu Ile Ser His Thr Gln Lys Ala Thr Leu Val Cys Leu Ala Thr
    130                 135                 140

Gly Phe Tyr Pro Asp His Val Glu Leu Ser Trp Trp Val Asn Gly Lys
145                 150                 155                 160

Glu Val His Ser Gly Val Cys Thr Asp Pro Gln Pro Leu Lys Glu Gln
                165                 170                 175

Pro Ala Leu Asn Asp Ser Arg Tyr Ala Leu Ser Ser Arg Leu Arg Val
            180                 185                 190

Ser Ala Thr Phe Trp Gln Asp Pro Arg Asn His Phe Arg Cys Gln Val
        195                 200                 205

Gln Phe Tyr Gly Leu Ser Glu Asn Asp Glu Trp Thr Gln Asp Arg Ala
    210                 215                 220

Lys Pro Val Thr Gln Ile Val Ser Ala Glu Ala Trp Gly Arg Ala Asp
225                 230                 235                 240

<210> SEQ ID NO 17
<211> LENGTH: 240
<212> TYPE: PRT
<213> ORGANISM: Artificial Sequence
<220> FEATURE:
<223> OTHER INFORMATION: Beta chain amino acid sequence of soluble TCR

<400> SEQUENCE: 17

Asn Ala Gly Val Thr Gln Thr Pro Lys Phe Arg Val Leu Lys Thr Gly
1               5                   10                  15

Gln Ser Met Thr Leu Leu Cys Ala Gln Asp Met Asn His Asp Tyr Met
            20                  25                  30

```
Tyr Trp Tyr Arg Gln Asp Pro Gly Met Gly Leu Arg Leu Ile His Tyr
             35                  40                  45
Ser Val Gly Glu Gly Thr Thr Ala Lys Gly Glu Val Pro Asp Gly Tyr
 50                  55                  60
Asn Val Ser Arg Leu Lys Lys Gln Asn Phe Leu Leu Gly Leu Glu Ser
 65                  70                  75                  80
Ala Ala Pro Ser Gln Thr Ser Val Tyr Phe Cys Ala Ser Ser Phe Thr
                 85                  90                  95
Asp Thr Gln Tyr Phe Gly Pro Gly Thr Arg Leu Thr Val Leu Glu Asp
            100                 105                 110
Leu Lys Asn Val Phe Pro Pro Glu Val Ala Val Phe Glu Pro Ser Glu
            115                 120                 125
Ala Glu Ile Ser His Thr Gln Lys Ala Thr Leu Val Cys Leu Ala Thr
        130                 135                 140
Gly Phe Tyr Pro Asp His Val Glu Leu Ser Trp Trp Val Asn Gly Lys
145                 150                 155                 160
Glu Val His Ser Gly Val Cys Thr Asp Pro Gln Pro Leu Lys Glu Gln
                165                 170                 175
Pro Ala Leu Asn Asp Ser Arg Tyr Ala Leu Ser Ser Arg Leu Arg Val
            180                 185                 190
Ser Ala Thr Phe Trp Gln Asn Pro Arg Asn His Phe Arg Cys Gln Val
            195                 200                 205
Gln Phe Tyr Gly Leu Ser Glu Asn Asp Glu Trp Thr Gln Asp Arg Ala
            210                 215                 220
Lys Pro Val Thr Gln Ile Val Ser Ala Glu Ala Trp Gly Arg Ala Asp
225                 230                 235                 240

<210> SEQ ID NO 18
<211> LENGTH: 1861
<212> TYPE: DNA
<213> ORGANISM: Artificial Sequence
<220> FEATURE:
<223> OTHER INFORMATION: DNA sequence for the parental MAGE A10 TCR gene

<400> SEQUENCE: 18
gctagccgcc accatgatga agtccctgcg ggtgctgctg gtcatcctgt ggctgcagct      60
gtcctgggtc tggtcccagc agaaagaggt ggagcagaac agcggccctc tgagcgtgcc     120
cgagggcgct atcgccagcc tgaactgcac ctacagcgac agaggcagcc agagcttctt     180
ctggtacaga cagtacagcg gcaagagccc cgagctgatc atgagcatct acagcaacgg     240
cgacaaagag gacggccggt tcaccgccca gctgaacaag gccagccagt acgtgtccct     300
gctgatccgg gacagccagc ccagcgacag cgccacctac ctgtgcgccg tgagaggcac     360
aggcagaagg gccctgacat ttggcagcgg caccagactg caggtgcagc caatattcaa     420
gaaccccgac cccgccgtgt accagctgcg ggacagcaag agcagcgaca gagcgtgtg      480 cctgttcacc gacttcgaca gccagaccaa cgtgtcccag agcaaggaca cgacgtgta      540 catcaccgac aagaccgtgc tggacatgcg gagcatggac ttcaagagca cagcgccgt      600 ggcctggtcc aacaagagcg acttcgcctg cgccaacgcc ttcaacaaca gcatcatccc     660
cgaggacacc ttttttcccca gccccgagag cagctgcgca gtcaaactgg tggagaagtc     720
cttcgagaca gacaccaacc tgaacttcca gaacctgagc gtgatcggct tcagaatcct     780
gctgctgaag gtggccggct tcaatctgct gatgaccctg cggctgtgga gcagcggcag     840
ccgggccaag agaagcggat ccggcgccac caacttcagc ctgctgaagc aggccggcga     900
```

```
cgtggaggaa aaccctggcc ctaggatgtc tctgggcctg ctgtgctgtg gcgtgttctc    960
cctgctgtgg gccggacctg tgaatgccgg cgtgacccag accccaagt tccgggtgct    1020 gaaaaccggc cagagcatga cactgctgtg cgcccaggac atgaaccacg agtacatgta    1080
ttggtacaga caggaccccg gcatgggcct gcggctgatc cactattctg tgggcgaggg    1140
caccaccgcc aagggcgaag tgcctgatgg ctacaacgtg tcccggctga agaagcagaa    1200
cttcctgctg ggcctggaaa gcgccgctcc tagccagacc agcgtgtact ctgcgccag    1260 cagcttcacc gacacccagt acttcggccc tggcaccaga ctgaccgtgc tggaggacct    1320
gaagaacgtg ttcccccag aggtggccgt gttcgagccc tctgaggccg agatcagcca    1380
cacccagaaa gccaccctgg tctgcctggc caccggcttc taccccgacc acgtggaact    1440
gtcttggtgg gtgaacggca agaggtgca gcgcggcgtc agcaccgacc ctcagcccct    1500
gaaagagcag cccgccctga cgacagccg gtactgcctg agcagcagac tgcgggtgtc    1560
cgccaccttc tggcagaacc cccggaacca cttcagatgc caggtgcagt tctacggcct    1620
gagcgagaac gacgagtgga cccaggaccg ggccaagcct gtgacccaga tcgtgtctgc    1680
cgaagcatgg gggcgcgccg attgcggctt cacaagcgag agctaccagc agggcgtgct    1740
gagcgccacc atcctgtacg agatcctgct gggcaaggcc accctgtacg ccgtgctggt    1800
gtccgctctg gtgctgatgg ccatggtgaa acggaaggac agccggggct aataagtcga    1860
c                                                                   1861

<210> SEQ ID NO 19
<211> LENGTH: 612
<212> TYPE: PRT
<213> ORGANISM: Artificial Sequence
<220> FEATURE:
<223> OTHER INFORMATION: Amino acid sequence of parental MAGE A10 TCR

<400> SEQUENCE: 19

Met Met Lys Ser Leu Arg Val Leu Leu Val Ile Leu Trp Leu Gln Leu
1               5                   10                  15

Ser Trp Val Trp Ser Gln Gln Lys Glu Val Glu Gln Asn Ser Gly Pro
            20                  25                  30

Leu Ser Val Pro Glu Gly Ala Ile Ala Ser Leu Asn Cys Thr Tyr Ser
        35                  40                  45

Asp Arg Gly Ser Gln Ser Phe Phe Trp Tyr Arg Gln Tyr Ser Gly Lys
    50                  55                  60

Ser Pro Glu Leu Ile Met Ser Ile Tyr Ser Asn Gly Asp Lys Glu Asp
65                  70                  75                  80

Gly Arg Phe Thr Ala Gln Leu Asn Lys Ala Ser Gln Tyr Val Ser Leu
                85                  90                  95

Leu Ile Arg Asp Ser Gln Pro Ser Asp Ser Ala Thr Tyr Leu Cys Ala
            100                 105                 110

Val Arg Gly Thr Gly Arg Arg Ala Leu Thr Phe Gly Ser Gly Thr Arg
        115                 120                 125

Leu Gln Val Gln Pro Asn Ile Gln Asn Pro Asp Pro Ala Val Tyr Gln
    130                 135                 140

Leu Arg Asp Ser Lys Ser Ser Asp Lys Ser Val Cys Leu Phe Thr Asp
145                 150                 155                 160

Phe Asp Ser Gln Thr Asn Val Ser Gln Ser Lys Asp Ser Asp Val Tyr
                165                 170                 175

Ile Thr Asp Lys Thr Val Leu Asp Met Arg Ser Met Asp Phe Lys Ser
            180                 185                 190
```

```
Asn Ser Ala Val Ala Trp Ser Asn Lys Ser Asp Phe Ala Cys Ala Asn
        195                 200                 205

Ala Phe Asn Asn Ser Ile Ile Pro Glu Asp Thr Phe Phe Pro Ser Pro
210                 215                 220

Glu Ser Ser Cys Asp Val Lys Leu Val Glu Lys Ser Phe Glu Thr Asp
225                 230                 235                 240

Thr Asn Leu Asn Phe Gln Asn Leu Ser Val Ile Gly Phe Arg Ile Leu
                245                 250                 255

Leu Leu Lys Val Ala Gly Phe Asn Leu Leu Met Thr Leu Arg Leu Trp
                260                 265                 270

Ser Ser Gly Ser Arg Ala Lys Arg Ser Gly Ser Gly Ala Thr Asn Phe
                275                 280                 285

Ser Leu Leu Lys Gln Ala Gly Asp Val Glu Glu Asn Pro Gly Pro Arg
                290                 295                 300

Met Ser Leu Gly Leu Leu Cys Cys Gly Val Phe Ser Leu Leu Trp Ala
305                 310                 315                 320

Gly Pro Val Asn Ala Gly Val Thr Gln Thr Pro Lys Phe Arg Val Leu
                325                 330                 335

Lys Thr Gly Gln Ser Met Thr Leu Leu Cys Ala Gln Asp Met Asn His
                340                 345                 350

Glu Tyr Met Tyr Trp Tyr Arg Gln Asp Pro Gly Met Gly Leu Arg Leu
                355                 360                 365

Ile His Tyr Ser Val Gly Glu Gly Thr Thr Ala Lys Gly Glu Val Pro
                370                 375                 380

Asp Gly Tyr Asn Val Ser Arg Leu Lys Lys Gln Asn Phe Leu Leu Gly
385                 390                 395                 400

Leu Glu Ser Ala Ala Pro Ser Gln Thr Ser Val Tyr Phe Cys Ala Ser
                405                 410                 415

Ser Phe Thr Asp Thr Gln Tyr Phe Gly Pro Gly Thr Arg Leu Thr Val
                420                 425                 430

Leu Glu Asp Leu Lys Asn Val Phe Pro Pro Glu Val Ala Val Phe Glu
                435                 440                 445

Pro Ser Glu Ala Glu Ile Ser His Thr Gln Lys Ala Thr Leu Val Cys
450                 455                 460

Leu Ala Thr Gly Phe Tyr Pro Asp His Val Glu Leu Ser Trp Trp Val
465                 470                 475                 480

Asn Gly Lys Glu Val His Ser Gly Val Ser Thr Asp Pro Gln Pro Leu
                485                 490                 495

Lys Glu Gln Pro Ala Leu Asn Asp Ser Arg Tyr Cys Leu Ser Ser Arg
                500                 505                 510

Leu Arg Val Ser Ala Thr Phe Trp Gln Asn Pro Arg Asn His Phe Arg
                515                 520                 525

Cys Gln Val Gln Phe Tyr Gly Leu Ser Glu Asn Asp Glu Trp Thr Gln
                530                 535                 540

Asp Arg Ala Lys Pro Val Thr Gln Ile Val Ser Ala Glu Ala Trp Gly
545                 550                 555                 560

Arg Ala Asp Cys Gly Phe Thr Ser Glu Ser Tyr Gln Gln Gly Val Leu
                565                 570                 575

Ser Ala Thr Ile Leu Tyr Glu Ile Leu Leu Gly Lys Ala Thr Leu Tyr
                580                 585                 590
```

```
Ala Val Leu Val Ser Ala Leu Val Leu Met Ala Met Val Lys Arg Lys
    595                 600                 605

Asp Ser Arg Gly
    610
```

T CELL RECEPTORS

RELATED APPLICATIONS AND INCORPORATION BY REFERENCE

This application is a continuation-in-part application of international patent application Serial No. PCT/GB2015/052938 filed 8 Oct. 2015, which published as PCT Publication No. WO 2016/055785 on 14 Apr. 2016, which claims benefit of GB patent application Ser. No. 1417803.2 filed 8 Oct. 2014 and U.S. provisional application Ser. No. 62/061,248 filed 8 Oct. 2014.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

FIELD OF THE INVENTION

The present invention relates to T cell receptors (TCRs) which bind the HLA-A*02 restricted peptide GLYDGMEHL (SEQ ID NO: 1) derived from the MAGE-A10 protein. The TCRs of the invention demonstrate excellent specificity profiles for this MAGE epitope.

BACKGROUND TO THE INVENTION

The GLYDGMEHL (SEQ ID No: 1) peptide corresponds to amino acid residue numbers 254-262 of the known MAGE-A10 protein which is expressed in many tumour types.

MAGE-A10 is one of the most immunogenic members of a large number of sequence-related MAGE cancer-testis antigen proteins. It is expressed by between one third to two thirds of a range of common solid tumour types (e.g., lung, liver and gastric metastases). In addition it is expressed by several less common tumour types (e.g., various squamous cell carcinomas).

Normal adult MAGE-A10 tissue expression is restricted to the immune-privileged sites of the placenta and sperm cells/testes.

A MAGE-A10 T cell antigen peptide GLYDGMEHL has been confirmed as being presented by HLA-A2 positive tumour cell lines via Mass Spectrometry.

Some MAGE gene family proteins are only expressed in germ cells and cancer (MAGE-A to MAGE-C families). Others are widely expressed in normal tissues (MAGE-D through to MAGE-H). All these MAGE protein families have a homologous region that is closely matched to the sequence of the MAGE-A10 GLYDGMEHL peptide.

Citation or identification of any document in this application is not an admission that such document is available as prior art to the present invention.

SUMMARY OF THE INVENTION

It is important to select TCR clinical candidates that are highly specific for the MAGE-A10 peptide/HLA-A2 antigen or at least bind to other MAGE family antigens with complementary normal tissue and tumour distributions.

In a first aspect, the present invention provides a T cell receptor (TCR) having the property of binding to GLYDGMEHL (SEQ ID No: 1) in complex with HLA-A*02 with a dissociation constant of from about 0.05 µM to about 10.0 µM when measured with surface plasmon resonance at 25° C. and at a pH between 7.1 and 7.5 using a soluble form of the TCR, wherein the TCR may comprise a TCR alpha chain variable domain and a TCR beta chain variable domain, and wherein the TCR variable domains form contacts with at least residues Y3 and E7 of GLYDGMEHL (SEQ ID No: 1).

In some embodiments, the alpha chain variable domain of the TCR may comprise an amino acid sequence that has at least 80% identity to the sequence of amino acid residues 1-111 of SEQ ID No: 4, and/or the beta chain variable domain may comprise an amino acid sequence that has at least 80% identity to the sequence of amino acid residues 1-111 of SEQ ID No: 5.

In a further aspect, the present invention provides a T cell receptor (TCR) having the property of binding to GLYDGMEHL (SEQ ID No: 1) in complex with HLA-A*02 and which may comprise a TCR alpha chain variable domain and a TCR beta chain variable domain, the alpha chain variable domain which may comprise an amino acid sequence that has at least 80% identity to the sequence of amino acid residues 1-111 of SEQ ID No: 4, and/or the beta chain variable domain which may comprise an amino acid sequence that has at least 80% identity to the sequence of amino acid residues 1-111 of SEQ ID No: 5.

The GLYDGMEHL HLA-A2 complex provides a cancer marker that the TCRs of the invention can target. The present invention provides such TCRs useful for the purpose of delivering cytotoxic or immune effector agents to the cancer cells and/or useful for use in adoptive therapy.

Accordingly, it is an object of the invention not to encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. § 112, first paragraph) or the EPO (Article 83 of the EPC), such that Applicants reserve the right and hereby disclose a disclaimer of any previously described product, process of making the product, or method of using the product. It may be advantageous in the practice of the invention to be in compliance with Art. 53(c) EPC and Rule 28(b) and (c) EPC. All rights to explicitly disclaim any embodiments that are the subject of any granted patent(s) of applicant in the lineage of this application or in any other lineage or in any prior filed application of any third party is explicitly reserved Nothing herein is to be construed as a promise.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

BRIEF DESCRIPTION OF THE DRAWINGS

The following detailed description, given by way of example, but not intended to limit the invention solely to the specific embodiments described, may best be understood in conjunction with the accompanying drawings.

FIG. 1a shows the amino acid sequence (SEQ ID No: 2) of the extracellular part of the alpha chain of a parental MAGE-10-specific TCR, and FIG. 1b shows the amino acid sequence (SEQ ID No: 3) of the extracellular part of the beta chain of a parental MAGE-A10-specific TCR beta chain amino acid sequence.

FIG. 2a shows the amino acid sequence (SEQ ID No: 4) of the alpha chain of a soluble TCR (referred to herein as the "reference TCR). The sequence is the same as that of FIG. 1 except that a cysteine (bold and underlined) is substituted for T162 of SEQ ID No: 1 (i.e. T48 of the TRAC constant region). FIG. 2b shows the amino acid sequence (SEQ ID No: 5) of the beta chain of a soluble TCR (referred to herein as the "reference TCR). The sequence is the same as that of FIG. 2 except that a cysteine (bold and underlined) is substituted for S169 (i.e. S57 of the TRBC2 constant region) and A187 is substituted for C187 and D201 is substituted for N201.

FIG. 3 shows the respective amino acid sequences (SEQ ID Nos: 6 and 7) of alpha chains which may be present in TCRs of the invention. The subsequences forming the CDR regions, or substantial parts of the CDR regions, are underlined.

FIG. 4 shows the respective amino acid sequences (SEQ ID Nos: 8, 9, 10 and 11) of beta chains which may be present in TCRs of the invention. The subsequences forming the CDR regions, or substantial parts of the CDR regions are underlined.

FIG. 5 shows the respective amino acid sequences (SEQ ID Nos: 12 and 13) of alpha chains which may be present in TCRs of the invention. Relative to the sequences shown in FIG. 3, introduced cysteines are shown bold and underlined.

FIG. 6 shows the respective amino acid sequences (SEQ ID Nos: 14 and 15) of beta chains which may be present in TCRs of the invention. Relative to the sequences shown in FIG. 4, introduced cysteines are shown bold and underlined. Also relative to FIG. 4. C187 has been mutated to A187 to eliminate an unapired cysteine in any alpha-beta TCR having these beta chains.

FIG. 7 (SEQ ID No: 18) gives the DNA sequence for the parental MAGE A10 TCR gene (alpha chain-2A-beta chain construct with the Porcine teschovirus-1 2A sequence)

FIG. 8 (SEQ ID No: 19) gives the amino acid sequence of the parental MAGE A10 TCR for T-cell transduction produced from the DNA sequence of FIG. 7. The Porcine teschovirus-1 2A sequence is bold and underlined.

DETAILED DESCRIPTION OF THE INVENTION

Figure 9:
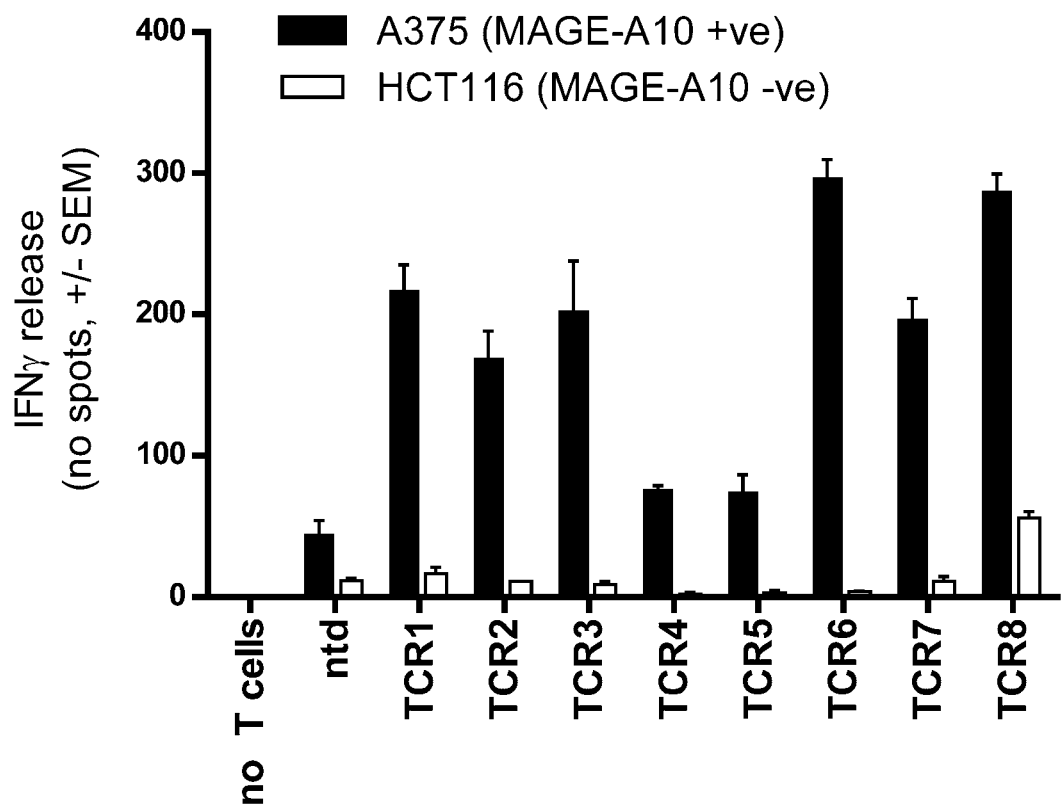
FIG. 9 is a graph showing the results of the activation of T cells in accordance with the invention.

TCRs are described using the International Immunogenetics (IMGT) TCR nomenclature, and links to the IMGT public database of TCR sequences. Native alpha-beta heterodimeric TCRs have an alpha chain and a beta chain. Broadly, each chain may comprise variable, joining and constant regions, and the beta chain also usually contains a short diversity region between the variable and joining regions, but this diversity region is often considered as part of the joining region. Each variable region comprises three CDRs (Complementarity Determining Regions) embedded in a framework sequence, one being the hypervariable region named CDR3. There are several types of alpha chain variable (Vα) regions and several types of beta chain variable (Vβ) regions distinguished by their framework, CDR1 and CDR2 sequences, and by a partly defined CDR3 sequence. The Vα types are referred to in IMGT nomenclature by a unique TRAV number. Thus "TRAV21" defines a TCR Vα region having unique framework and CDR1 and CDR2 sequences, and a CDR3 sequence which is partly defined by an amino acid sequence which is preserved from TCR to TCR but which also includes an amino acid sequence which varies from TCR to TCR. In the same way, "TRBV5-1" defines a TCR Vβ region having unique framework and CDR1 and CDR2 sequences, but with only a partly defined CDR3 sequence.

The joining regions of the TCR are similarly defined by the unique IMGT TRAJ and TRBJ nomenclature, and the constant regions by the IMGT TRAC and TRBC nomenclature.

The beta chain diversity region is referred to in IMGT nomenclature by the abbreviation TRBD, and, as mentioned, the concatenated TRBD/TRBJ regions are often considered together as the joining region.

The α and β chains of αβ TCR's are generally regarded as each having two "domains", namely variable and constant domains. The variable domain consists of a concatenation of variable region and joining region. In the present specification and claims, the term "TCR alpha variable domain" therefore refers to the concatenation of TRAV and TRAJ regions, and the term TCR alpha constant domain refers to the extracellular TRAC region, or to a C-terminal truncated TRAC sequence. Likewise the term "TCR beta variable domain" refers to the concatenation of TRBV and TRBD/TRBJ regions, and the term TCR beta constant domain refers to the extracellular TRBC region, or to a C-terminal truncated TRBC sequence.

The unique sequences defined by the IMGT nomenclature are widely known and accessible to those working in the TCR field. For example, they can be found in the IMGT public database. The "T cell Receptor Factsbook", (2001) LeFranc and LeFranc, Academic Press, ISBN 0-12-441352-8 also discloses sequences defined by the IMGT nomenclature, but because of its publication date and consequent time-lag, the information therein sometimes needs to be confirmed by reference to the IMGT database.

One TCR in accordance with the invention may comprise an alpha chain extracellular domain as shown in SEQ ID No: 2 and a beta chain extracellular domain as shown in SEQ ID No: 3. The terms "parental TCR", "parental MAGE-A10 TCR", are used synonymously herein to refer to this TCR which may comprise the extracellular alpha and beta chain of SEQ ID Nos: 2 and 3 respectively. It is desirable to provide TCRs that are mutated or modified relative to the parental TCR that have a higher affinity and/or a slower off-rate for the peptide-HLA complex than the parental TCR.

For the purpose of providing a reference TCR against which the binding profile of such mutated or modified TCRs may be compared, it is convenient to use a soluble TCR in accordance with the invention having the extracellular sequence of the parental MAGE-A10 TCR alpha chain given in FIG. 2a (SEQ ID No: 4) and the extracellular sequence of the parental MAGE-A10 TCR beta chain given in FIG. 2b (SEQ ID No: 5). That TCR is referred to herein as the "the reference TCR" or "the reference MAGE-A10 TCR". Note that SEQ ID No: 4 is the parental alpha chain extracellular sequence of SEQ ID No: 2 except that C162 has been substituted for T162 (i.e. T48 of TRAC). Likewise SEQ ID No: 5 is the parental beta chain extracellular sequence of SEQ ID No: 3 except that C169 has been substituted for S169 (i.e. S57 of TRBC2), A187 has been substituted for C187 and D201 has been substituted for N201. These cysteine substitutions relative to the parental alpha and beta chain extracellular sequences enable the formation of an interchain disulfide bond which stabilises the refolded soluble TCR, i.e. the TCR formed by refolding extracellular alpha and beta chains. Use of the stable disulfide linked soluble TCR as the reference TCR enables more convenient assessment of binding affinity and binding half life. TCRs of the invention may comprise the mutations described above.

TCRs of the invention may be non-naturally occurring and/or purified and/or engineered. TCRs of the invention may have more than one mutation present in the alpha chain variable domain and/or the beta chain variable domain relative to the parental TCR. "Engineered TCR" and "mutant TCR" are used synonymously herein and generally mean a TCR which has one or more mutations introduced relative to the parental TCR, in particular in the alpha chain variable domain and/or the beta chain variable domain thereof. These mutation(s) may improve the binding affinity for GLYDGMEHL (SEQ ID No: 1) in complex with HLA-A*02. In certain embodiments, there are 1, 2, 3, 4, 5, 6, 7 or 8 mutations in alpha chain variable domain, for example 4 or 8 mutations, and/or 1, 2, 3, 4 or 5 mutations in the beta chain variable domain, for example 5 mutations. In some embodiments, the α chain variable domain of the TCR of the invention may comprise an amino acid sequence that has at least 90%, at least 91%, at least 92%, at least 93%, at least 94%, at least 95%, at least 96%, at least 97%, at least 98% or at least 99% identity to the sequence of amino acid residues 1-111 of SEQ ID No: 4. In some embodiments, the 0 chain variable domain of the TCR of the invention may comprise an amino acid sequence that has at least 90%, at least 91%, at least 92%, at least 93%, at least 94%, at least 95%, at least 96%, at least 97%, at least 98% or at least 99% identity to the sequence of amino acid residues 1-111 of SEQ ID No: 5.

The alpha chain variable domain of a TCR of the invention may have the following mutation:

| Q31 | A or S |
|---|---| with reference to the numbering shown in SEQ ID No: 4, and/or the beta chain variable domain may have at least one of the following mutations:

| E30 | D |
|---|---|
| G51 | S, A or F | with reference to the numbering shown in SEQ ID No: 5.

The alpha chain variable domain of a TCR of the invention may comprise the amino acid sequence of amino acid residues 1-111 of SEQ ID No: 6 or 12 or an amino acid sequence in which amino acid residues 1-26, 33-49, 55-89 and 94-111 thereof have at least 90% or 95% identity to the sequence of amino acid residues 1-26, 33-49, 55-89 and 94-111 respectively of SEQ ID No: 6 or 12 and in which amino acid residues 27-32, 50-54 and 90-93 have at least 90% or 95% identity to the sequence of amino acid residues 27-32, 50-54 and 90-93 respectively of SEQ ID No: 6 or 12.

Alternatively, the alpha chain variable domain may comprise the amino acid sequence of amino acid residues 1-111 SEQ ID No: 7 or 13 or an amino acid sequence in which amino acid residues 1-26, 33-49, 55-89 and 94-111 thereof have at least 90% or 95% identity to the sequence of amino acid residues 1-26, 33-49, 55-89 and 94-111 respectively of SEQ ID No: 7 or 13 and in which amino acid residues 27-32, 50-54 and 90-93 have at least 90% or 95% identity to the sequence of amino acid residues 27-32, 50-54 and 90-93 respectively of SEQ ID No: 7 or In the alpha chain variable domain, the sequence of amino acid residues 1-26 thereof may have (a) at least 90% identity to the sequence of amino acid residues 1-26 of SEQ ID No: 4 or (b) may have one, two or three amino acid residues inserted or deleted relative to the sequence of (a);

(ii) amino acid residues 27-32 may be DRGSQS, DRGSAS or DRGSSS;

(iii) amino acid residues 33-49 thereof may have (a) at least 90% identity to the sequence of amino acid residues 33-49 of SEQ ID NO: 4 or (b) may have one, two or three amino acid residues inserted or deleted relative to the sequence of (a);

(iv) amino acid residues 50-54 may be IYSNG (v) amino acid residues 55-89 thereof may have at least 90% identity to the sequence of amino acid residues 55-89 of SEQ ID No: 4 or may have one, two or three insertions, deletions or substitutions relative thereto;

(vi) amino acids 90-93 may be AVRG; and (vii) amino acid residues 94-111 thereof has at least 90% identity to the sequence of amino acid residues 94-111 of SEQ ID No: 4 or may have one, two or three insertions, deletions or substitutions relative thereto.

The beta chain variable domain of a TCR of the invention may comprise the amino acid sequence of SEQ ID No: 8 or 14 or an amino acid sequence in which amino acid residues 1-26, 32-48, 54-90 and 96-111 thereof have at least 90% or 95% identity to the sequence of amino acid residues 1-26, 32-48, 54-90 and 96-111 respectively of SEQ ID No: 8 or 14 and in which amino acid residues 27-31, 49-53 and 91-95 have at least 90% or 95% identity to the sequence of amino acid residues 27-31, 49-53 and 91-95 respectively of SEQ ID No: 8 or 14.

Alternatively, the beta chain variable domain of a TCR of the invention may comprise the amino acid sequence of SEQ ID No: 9 or 15 or an amino acid sequence in which amino acid residues 1-26, 32-48, 54-90 and 96-111 thereof have at least 90% or 95% identity to the sequence of amino acid residues 1-26, 32-48, 54-90 and 96-111 respectively of SEQ ID No: 9 or 15 and in which amino acid residues 27-31, 49-53 and 91-95 have at least 90% or 95% identity to the sequence of amino acid residues 27-31, 49-53 and 91-95 respectively of SEQ ID No: 9 or 15.

Alternatively, the beta chain variable domain of a TCR of the invention may comprise the amino acid sequence of SEQ ID No: 10 or 16 or an amino acid sequence in which amino acid residues 1-26, 32-48, 54-90 and 96-111 thereof have at least 90% or 95% identity to the sequence of amino acid residues 1-26, 32-48, 54-90 and 96-111 respectively of SEQ ID No: 10 or 16 and in which amino acid residues 27-31, 49-53 and 91-95 have at least 90% or 95% identity to the sequence of amino acid residues 27-31, 49-53 and 91-95 respectively of SEQ ID No: 10 or 16.

Alternatively, the beta chain variable domain of a TCR of the invention may comprise the amino acid sequence of SEQ ID No: 11 or 17 or an amino acid sequence in which amino acid residues 1-26, 32-48, 54-90 and 96-111 thereof have at least 90% or 95% identity to the sequence of amino acid residues 1-26, 32-48, 54-90 and 96-111 respectively of SEQ ID No: 11 or 17 and in which amino acid residues 27-31, 49-53 and 91-95 have at least 90% or 95% identity to the sequence of amino acid residues 27-31, 49-53 and 91-95 respectively of SEQ ID No: 11 or 17.

In the beta chain variable domain, the sequence of amino acid residues 1-26 thereof may have (a) at least 90% identity to the amino acid sequence of residues 1-26 of SEQ ID No: 5 or (b) may have one, two or three amino acid residues inserted or deleted relative to the sequence of (a);
  (ii) amino acid residues 27-31 may be MNHEY or MNHDY;
  (iii) amino acid residues 32-48 thereof may have (a) at least 90% identity to the sequence of amino acid residues 32-48 of SEQ ID NO: 5 or (b) may have one, two or three amino acid residues inserted or deleted relative to the sequence of (a);
  (iv) amino acid residues 49-53 may be SVGEG, SVSEG, SVAEG or SVFEG;
  (v) amino acid residues 54-90 thereof may have (a) at least 90% identity to the sequence of amino acid residues 54-90 of SEQ ID NO: 5 or (b) may have one, two or three amino acid residues inserted or deleted relative to the sequence of (a);
  (vi) amino acids 91-95 may be CASSF;
  (vii) amino acid residues 96-111 thereof may have at least 90% identity to the sequence of amino acid residues 96-111 of SEQ ID NO: 5 or may have one, two or three insertions, deletions or substitutions relative thereto.

A TCR of the invention may have one of the following combinations of alpha and beta chain variable domains:

| Alpha Chain SEQ ID No | Beta Chain SEQ ID No |
|---|---|
| 2 | 3 |
| 2 | 5 |
| 2 | 8 |
| 2 | 9 |
| 2 | 10 |
| 2 | 11 |
| 2 | 14 |
| 2 | 15 |
| 2 | 16 |
| 2 | 17 |
| 4 | 3 |
| 4 | 5 |
| 4 | 8 |
| 4 | 9 |
| 4 | 10 |
| 4 | 11 |
| 4 | 14 |
| 4 | 15 |
| 4 | 16 |
| 4 | 17 |
| 6 | 3 |
| 6 | 5 |
| 6 | 8 |
| 6 | 9 |
| 6 | 10 |
| 6 | 11 |
| 6 | 14 |
| 6 | 15 |
| 6 | 16 |
| 6 | 17 |
| 7 | 3 |
| 7 | 5 |
| 7 | 8 |
| 7 | 9 |
| 7 | 10 |
| 7 | 11 |
| 7 | 14 |
| 7 | 15 |
| 7 | 16 |
| 7 | 17 |
| 12 | 3 |
| 12 | 5 |
| 12 | 8 |
| 12 | 9 |
| 12 | 10 |
| 12 | 11 |
| 12 | 14 |
| 12 | 15 |
| 12 | 16 |
| 12 | 17 |
| 13 | 3 |
| 13 | 5 |
| 13 | 8 |
| 13 | 9 |
| 13 | 10 |
| 13 | 11 |
| 13 | 14 |
| 13 | 15 |
| 13 | 16 |
| 13 | 17 |

Within the scope of the invention are phenotypically silent variants of any TCR of the invention disclosed herein. As used herein the term "phenotypically silent variants" is understood to refer to a TCR which incorporates one or more further amino acid changes in addition to those set out above which TCR has a similar phenotype to the corresponding TCR without said change(s). For the purposes of this application, TCR phenotype may comprise antigen binding specificity ($K_D$ and/or binding half life) and antigen specificity. A phenotypically silent variant may have a $K_D$ and/or binding half-life for the GLYDGMEHL (SEQ ID No: 1) HLA-A*02 complex within 10% of the measured $K_D$ and/or binding half-life of the corresponding TCR without said change(s), when measured under identical conditions (for example at 25° C. and on the same SPR chip). Suitable conditions are further defined in Example 3. Antigen specificity is further defined below. As is known to those skilled in the art, it may be possible to produce TCRs that incorporate changes in the constant and/or variable domains thereof compared to those detailed above without altering the affinity for the interaction with the GLYDGMEHL (SEQ ID No: 1) HLA-A*02 complex. In particular, such silent mutations may be incorporated within parts of the sequence that are known not to be directly involved in antigen binding (e.g. outside the CDRs). Such trivial variants are included in the scope of this invention. Those TCRs in which one or more conservative substitutions have been made also form part of this invention.

Mutations can be carried out using any appropriate method including, but not limited to, those based on polymerase chain reaction (PCR), restriction enzyme-based cloning, or ligation independent cloning (LIC) procedures. These methods are detailed in many of the standard molecular biology texts. For further details regarding polymerase chain reaction (PCR) and restriction enzyme-based cloning, see Sambrook & Russell, (2001) Molecular Cloning—A Laboratory Manual (3$^{rd}$ Ed.) CSHL Press. Further information on ligation independent cloning (LIC) procedures can be found in Rashtchian, (1995) *Curr Opin Biotechnol* 6(1): 30-6.

The TCRs of the invention have the property of binding the MAGE-A10 peptide, GLYDGMEHL (SEQ ID No: 1) HLA-A2 complex. The TCRs of the invention have been found to be highly specific for those MAGE epitopes relative to other, irrelevant epitopes, and are thus particularly suitable as targeting vectors for delivery of therapeutic agents or detectable labels to cells and tissues displaying those epitopes. Specificity in the context of TCRs of the invention relates to their ability to recognise HLA-A*02 target cells that are positive for the peptide GLYDGMEHL, whilst having minimal ability to recognise HLA-A*02 target cells that are negative for the peptide. To test specificity, the TCRs may be in soluble form and/or may be expressed on the surface of T cells. Recognition may be determined by measuring the level of T cell activation in the presence of a TCR and target cells. In this case, minimal recognition of peptide negative target cells is defined as a level of T cell activation of less than 10%, preferably less than 5%, and more preferably less than 1%, of the level produced in the presence of peptide positive target cells, when measured under the same conditions. For soluble TCRs of the invention, specificity may be determined at a therapeutically relevant TCR concentration. A therapeutically relevant concentration may be defined as a TCR concentration of $10^{-9}$ M or below, and/or a concentration of up to 100, preferably up to 1000, fold greater than the corresponding EC50 value. Peptide positive cells may be obtained by peptide-pulsing or, more preferably, they may naturally present said peptide. Preferably, both peptide positive and peptide negative cells are human cells.

Certain TCRs of the invention have been found to be highly suitable for use in adoptive therapy. Such TCRs may have a $K_D$ for the complex of less than the 200 μM, for example from about 0.05 μM to about 100 μM and/or have a binding half-life (T½) for the complex in the range of from about 0.5 seconds to about 12 minutes. In some embodiments, TCRs of the invention may have a $K_D$ for the complex of from about 0.05 μM to about 10 μM, about 0.1 μM to about 5 μM or about 0.1 μM to about 2 μM. Without wishing to be bound by theory, there seems to be an optimum window of affinity for TCRs with therapeutic use in adoptive cell therapy. Naturally occurring TCRs recognising epitopes from tumour antigens are generally of too low affinity (20 microM to 50 microM) and very high affinity TCRs (in the nanomolar range or higher) suffer from cross reactivity issues (Robbins et al (2008) J. Immunol. 180 6116-6131; Zhao et al (2007) J. Immunol. 179 5845-5854; Scmid et al (2010) J. Immunol 184 4936-4946)

The TCRs of the invention may be αβ heterodimers or may be in single chain format. Single chain formats include αβ TCR polypeptides of the Vα-L-Vβ, Vβ-L-Vα, Vα-Cα-L-Vβ or Vα-L-Vβ-Cβ types, wherein Vα and Vβ are TCR α and β variable regions respectively, Cα and Cβ are TCR α and β constant regions respectively, and L is a linker sequence. For use as a targeting agent for delivering therapeutic agents to the antigen presenting cell the TCR may be in soluble form (i.e. having no transmembrane or cytoplasmic domains). For stability, soluble αβ heterodimeric TCRs preferably have an introduced disulfide bond between residues of the respective constant domains, as described, for example, in WO 03/020763. One or both of the constant domains present in an αβ heterodimer of the invention may be truncated at the C terminus or C termini, for example by up to 15, or up to 10 or up to 8 or fewer amino acids. For use in adoptive therapy, an αβ heterodimeric TCR may, for example, be transfected as full length chains having both cytoplasmic and transmembrane domains. TCRs for use in adoptive therapy may contain a disulphide bond corresponding to that found in nature between the respective alpha and beta constant domains, additionally or alternatively a non-native disulphide bond may be present.

As will be obvious to those skilled in the art, it may be possible to truncate the sequences provided at the C-terminus and/or N-terminus thereof, by 1, 2, 3, 4, 5 or more residues, without substantially affecting the binding characteristics of the TCR. All such trivial variants are encompassed by the present invention.

Alpha-beta heterodimeric TCRs of the invention usually comprise an alpha chain TRAC constant domain sequence and a beta chain TRBC1 or TRBC2 constant domain sequence. The alpha and beta chain constant domain sequences may be modified by truncation or substitution to delete the native disulfide bond between Cys4 of exon 2 of TRAC and Cys2 of exon 2 of TRBC1 or TRBC2. The alpha and beta chain constant domain sequences may also be modified by substitution of cysteine residues for Thr 48 of TRAC and Ser 57 of TRBC1 or TRBC2, the said cysteines forming a disulfide bond between the alpha and beta constant domains of the TCR.

Some TCRs of the invention have a binding affinity for, and/or a binding half-life for, the GLYDGMEHL-HLA-A2 complex substantially higher than that of the reference MAGE-A10 TCR, Increasing the binding affinity of a native TCR often reduces the specificity of the TCR for its peptide-MHC ligand, and this is demonstrated in Zhao Yangbing et al., The Journal of Immunology, The American Association of Immunologists, US, vol. 179, No. 9, 1 Nov. 2007, 5845-5854. However, the TCRs of the invention which are derived from the parental TCR remain specific for the GLYDGMEHL-HLA-A2 complex, despite having substantially higher binding affinity than the parental TCR.

Binding affinity (inversely proportional to the equilibrium constant $K_D$) and binding half-life (expressed as T½) can be determined using the Surface Plasmon Resonance (BIAcore) method of Example 3 herein. Measurements may be carried out at 25° C. and at a pH between 7.1 and 7.5 using a soluble version of the TCR. It will be appreciated that doubling the affinity of a TCR results in halving the $K_D$. T½ is calculated as ln 2 divided by the off-rate ($k_{off}$). So doubling of T½ results in a halving in $k_{off}$. $K_D$ and $k_{off}$ values for TCRs are usually measured for soluble forms of the TCR, i.e. those forms which are truncated to remove hydrophobic transmembrane domain residues. Therefore it is to be understood that a given TCR meets the requirement that it has a binding affinity for, and/or a binding half-life for, the GLYDGMEHL-HLA-A2 complex if a soluble form of that TCR meets that requirement. Preferably the binding affinity or binding half-life of a given TCR is measured several times, for example 3 or more times, using the same assay protocol, and an average of the results is taken. The reference MAGE-A10 TCR has a $K_D$ of approximately 2 μM as measured by that method, and its $k_{off}$ is approximately) 0.73 s$^{-1}$ (i.e T½ is approximately 0.95 s).

In a further aspect, the present invention provides nucleic acid encoding a TCR of the invention. In some embodiments, the nucleic acid is cDNA. In some embodiments, the invention provides nucleic acid which may comprise a sequence encoding an α chain variable domain of a TCR of the invention. In some embodiments, the invention provides nucleic acid which may comprise a sequence encoding a β chain variable domain of a TCR of the invention. The nucleic acid may be non-naturally occurring and/or purified and/or engineered.

In another aspect, the invention provides a vector which may comprise nucleic acid of the invention. Preferably the vector is a TCR expression vector.

The invention also provides a cell harbouring a vector of the invention, preferably a TCR expression vector. The vector may comprise nucleic acid of the invention encoding in a single open reading frame, or two distinct open reading frames, the alpha chain and the beta chain respectively. Another aspect provides a cell harbouring a first expression vector which may comprise nucleic acid encoding the alpha chain of a TCR of the invention, and a second expression vector which may comprise nucleic acid encoding the beta chain of a TCR of the invention. Such cells are particularly useful in adoptive therapy. The cells of the invention may be isolated and/or recombinant and/or non-naturally occurring and/or engineered.

Since the TCRs of the invention have utility in adoptive therapy, the invention includes a non-naturally occurring and/or purified and/or or engineered cell, especially a T-cell, presenting a TCR of the invention. The invention also provides an expanded population of T cells presenting a TCR of the invention. There are a number of methods suitable for the transfection of T cells with nucleic acid (such as DNA, cDNA or RNA) encoding the TCRs of the invention (see for example Robbins et al., (2008) *J Immunol.* 180: 6116-6131). T cells expressing the TCRs of the invention will be suitable for use in adoptive therapy-based treatment of cancer. As will be known to those skilled in the art, there are a number of suitable methods by which adoptive therapy can be carried out (see for example Rosenberg et al., (2008) *Nat Rev Cancer* 8(4): 299-308).

Soluble TCRs of the invention are useful for delivering detectable labels or therapeutic agents to the antigen presenting cells and tissues containing the antigen presenting cells. The may therefore be associated (covalently or otherwise) with a detectable label (for diagnostic purposes wherein the TCR is used to detect the presence of cells presenting the GLYDGMEHL-HLA-A2 complex); a therapeutic agent; or a PK modifying moiety (for example by PEGylation).

Detectable labels for diagnostic purposes include for instance, fluorescent labels, radiolabels, enzymes, nucleic acid probes and contrast reagents.

Therapeutic agents which may be associated with the TCRs of the invention include immunomodulators, radioactive compounds, enzymes (perforin for example) or chemotherapeutic agents (cisplatin for example). To ensure that toxic effects are exercised in the desired location the toxin could be inside a liposome linked to TCR so that the compound is released slowly. This will prevent damaging effects during the transport in the body and ensure that the toxin has maximum effect after binding of the TCR to the relevant antigen presenting cells.

Other suitable therapeutic agents include:
  small molecule cytotoxic agents, i.e. compounds with the ability to kill mammalian cells having a molecular weight of less than 700 Daltons. Such compounds could also contain toxic metals capable of having a cytotoxic effect. Furthermore, it is to be understood that these small molecule cytotoxic agents also include pro-drugs, i.e. compounds that decay or are converted under physiological conditions to release cytotoxic agents. Examples of such agents include cis-platin, maytansine derivatives, rachelmycin, calicheamicin, docetaxel, etoposide, gemcitabine, ifosfamide, irinotecan, melphalan, mitoxantrone, sorfimer sodiumphotofrin II, temozolomide, topotecan, trimetreate glucuronate, auristatin E vincristine and doxorubicin;
  peptide cytotoxins, i.e. proteins or fragments thereof with the ability to kill mammalian cells. For example, ricin, diphtheria toxin, *pseudomonas* bacterial exotoxin A, DNase and RNase;
  radio-nuclides, i.e. unstable isotopes of elements which decay with the concurrent emission of one or more of α or β particles, or γ rays. For example, iodine 131, rhenium 186, indium 111, yttrium 90, bismuth 210 and 213, actinium 225 and astatine 213; chelating agents may be used to facilitate the association of these radio-nuclides to the high affinity TCRs, or multimers thereof;
  immuno-stimulants, i.e. immune effector molecules which stimulate immune response. For example, cytokines such as IL-2 and IFN-γ,
  Superantigens and mutants thereof;
  TCR-HLA fusions;
  chemokines such as IL-8, platelet factor 4, melanoma growth stimulatory protein, etc;
  antibodies or fragments thereof, including anti-T cell or NK cell determinant antibodies (e.g. anti-CD3, anti-CD28 or anti-CD16);
  alternative protein scaffolds with antibody like binding characteristics
  complement activators;
  xenogeneic protein domains, allogeneic protein domains, viral/bacterial protein domains, viral/bacterial peptides.

One preferred embodiment is provided by a TCR of the invention associated (usually by fusion to an N- or C-terminus of the alpha or beta chain) with an anti-CD3 antibody, or a functional fragment or variant of said anti-CD3 antibody. Antibody fragments and variants/analogues which are suitable for use in the compositions and methods described herein include minibodies, Fab fragments, F(ab')$_2$ fragments, dsFv and scFv fragments, Nanobodies™ (these constructs, marketed by Ablynx (Belgium), comprise synthetic single immunoglobulin variable heavy domain derived from a camelid (e.g. camel or llama) antibody) and Domain Antibodies (Domantis (Belgium), comprising an affinity matured single immunoglobulin variable heavy domain or immunoglobulin variable light domain) or alternative protein scaffolds that exhibit antibody like binding characteristics such as Affibodies (Affibody (Sweden), comprising engineered protein A scaffold) or Anticalins (Pieris (German), comprising engineered anticalins) to name but a few.

For some purposes, the TCRs of the invention may be aggregated into a complex which may comprise several TCRs to form a multivalent TCR complex. There are a number of human proteins that contain a multimerisation domain that may be used in the production of multivalent TCR complexes. For example the tetramerisation domain of p53 which has been utilised to produce tetramers of scFv antibody fragments which exhibited increased serum persistence and significantly reduced off-rate compared to the monomeric scFv fragment. (Willuda et al. (2001) J. Biol. Chem. 276 (17) 14385-14392). Haemoglobin also has a tetramerisation domain that could potentially be used for this kind of application. A multivalent TCR complex of the invention may have enhanced binding capability for the GLYDGMEHL HLA-A2 complex compared to a non-multimeric wild-type or T cell receptor heterodimer of the invention. Thus, multivalent complexes of TCRs of the invention are also included within the invention. Such multivalent TCR complexes according to the invention are particularly useful for tracking or targeting cells presenting particular antigens in vitro or in vivo, and are also useful as intermediates for the production of further multivalent TCR complexes having such uses.

As is well-known in the art, TCRs may be subject to post translational modifications. Glycosylation is one such modification, which comprises the covalent attachment of oligosaccharide moieties to defined amino acids in the TCR chain. For example, asparagine residues, or serine/threonine residues are well-known locations for oligosaccharide attachment. The glycosylation status of a particular protein depends on a number of factors, including protein sequence, protein conformation and the availability of certain enzymes. Furthermore, glycosylation status (i.e. oligosaccharide type, covalent linkage and total number of attachments) can influence protein function. Therefore, when producing recombinant proteins, controlling glycosylation is often desirable. Controlled glycosylation has been used to improve antibody based therapeutics. (Jefferis R., Nat Rev Drug Discov. 2009 March; 8(3):226-34.). For soluble TCRs of the invention glycosylation may be controlled in vivo, by using particular cell lines for example, or in vitro, by chemical modification. Such modifications are desirable, since glycosylation can improve phamacokinetics, reduce immunogenicity and more closely mimic a native human protein (Sinclair A M and Elliott S., Pharm Sci. 2005 August; 94(8):1626-35).

For administration to patients, the TCRs, nucleic acids and/or cells of the invention (usually associated with a detectable label or therapeutic agent), may be provided in a pharmaceutical composition together with a pharmaceutically acceptable carrier or excipient. Therapeutic or imaging TCRs in accordance with the invention will usually be supplied as part of a sterile, pharmaceutical composition which will normally include a pharmaceutically acceptable carrier. This pharmaceutical composition may be in any suitable form, (depending upon the desired method of administering it to a patient). It may be provided in unit dosage form, will generally be provided in a sealed container and may be provided as part of a kit. Such a kit would normally (although not necessarily) include instructions for use. It may include a plurality of said unit dosage forms.

The pharmaceutical composition may be adapted for administration by any appropriate route, preferably a parenteral (including subcutaneous, intramuscular, or preferably intravenous) route. Such compositions may be prepared by any method known in the art of pharmacy, for example by mixing the active ingredient with the carrier(s) or excipient(s) under sterile conditions.

Dosages of the substances of the present invention can vary between wide limits, depending upon the disease or disorder to be treated, the age and condition of the individual to be treated, etc. and a physician will ultimately determine appropriate dosages to be used.

TCRs, pharmaceutical compositions, vectors, nucleic acids and cells of the invention may be provided in substantially pure form, for example at least 80%, at least 85%, at least 90%, at least 91%, at least 92%, at least 93%, at least 94%, at least 95%, at least 96%, at least 97%, at least 98%, at least 99% or 100% pure.

Also provided by the invention are:
A TCR, nucleic acid or cell of the invention for use in medicine, preferably for use in a method of treating cancer, such as solid tumours (e.g., lung, liver and gastric metastases) and/or squamous cell carcinomas.
the use of a TCR, nucleic acid or cell of the invention in the manufacture of a medicament for treating cancer.
a method of treating cancer in a patient, which may comprise administering to the patient a TCR, nucleic acid or cell of the invention.

Preferred features of each aspect of the invention are as for each of the other aspects mutatis mutandis.

Although the present invention and its advantages have been described in detail, it should be understood that various changes, substitutions and alterations can be made herein without departing from the spirit and scope of the invention as defined in the appended claims.

The present invention will be further illustrated in the following Examples which are given for illustration purposes only and are not intended to limit the invention in any way.

EXAMPLES

Example 1—Cloning of the Reference MAGE-A10 TCR Alpha and Beta Chain Variable Region Sequences into pGMT7-Based Expression Plasmids The parental MAGE-A10 TCR variable alpha and TCR variable beta domains of SEQ ID NOS: 2 and 3 respectively were cloned into pGMT7-based expression plasmids containing either Cα or Cβ by standard methods described in (Molecular Cloning a Laboratory Manual Third edition by Sambrook and Russell). Plasmids were sequenced using an Applied Biosystems 3730xl DNA Analyzer. The reference MAGE-A10 TCR variable alpha and TCR variable beta domains of SEQ ID NOS: 4 and 5 respectively were cloned in the same way.

The DNA sequence encoding the TCR alpha chain variable region was ligated into pEX956, which was cut with Nde1 and Xho1. The DNA sequence encoding the TCR beta chain variable region was ligated into pEXb21, which was also cut with Nde1 and Xho1.

Ligated plasmids were transformed into competent *E. coli* strain XL1-blue cells and plated out on LB/agar plates containing 100 μg/mL ampicillin. Following incubation overnight at 37° C., single colonies were picked and grown in 5 mL LB containing 100 μg/mL ampicillin overnight at 37° C. with shaking. Cloned plasmids were purified using a Miniprep kit (Qiagen) and the plasmids were sequenced using an Applied Biosystems 3730xl DNA Analyzer.

Example 2—Expression, Refolding and Purification of Soluble Reference MAGE-A10 TCR The expression plasmids containing the reference TCR α-chain and β-chain respectively, as prepared in Example 1, were transformed separately into *E. coli* strain BL21pLysS, and single ampicillin-resistant colonies were grown at 37° C. in TYP (ampicillin 100 μg/ml) medium to $OD_{600}$ of ~0.6-0.8 before inducing protein expression with 0.5 mM IPTG. Cells were harvested three hours post-induction by centrifugation for 30 minutes at 4000 rpm in a Beckman J-6B. Cell pellets were lysed with 25 ml Bug Buster (NovaGen) in the presence of $MgCl_2$ and DNaseI. Inclusion body pellets were recovered by centrifugation for 30 minutes at 13000 rpm in a Beckman J2-21 centrifuge. Three detergent washes were then carried out to remove cell debris and membrane components. Each time the inclusion body pellet was homogenised in a Triton buffer (50 mM Tris-HCl pH 8.0, 0.5% Triton-X100, 200 mM NaCl, 10 mM NaEDTA,) before being pelleted by centrifugation for 15 minutes at 13000 rpm in a Beckman J2-21. Detergent and salt was then removed by a similar wash in the following buffer: 50 mM Tris-HCl pH 8.0, 1 mM NaEDTA. Finally, the inclusion bodies were divided into 30 mg aliquots and frozen at −70° C. Inclusion body protein yield was quantified by solubilising with 6 M guanidine-HCl and an OD measurement was taken on a Hitachi U-2001 Spectrophotometer. The protein concentration was then calculated using the extinction coefficient.

Approximately 15 mg of TCR α chain and 15 mg of TCR β chain solubilised inclusion bodies were thawed from frozen stocks and diluted into 10 ml of a guanidine solution (6 M Guanidine-hydrochloride, 50 mM Tris HCl pH 8.1, 100 mM NaCl, 10 mM EDTA, 10 mM DTT), to ensure complete chain denaturation. The guanidine solution containing fully reduced and denatured TCR chains was then injected into 0.5 litre of the following refolding buffer: 100 mM Tris pH 8.1, 400 mM L-Arginine, 2 mM EDTA, 5 M Urea. The redox couple (cysteamine hydrochloride and cystamine dihydrochloride) to final concentrations of 6.6 mM and 3.7 mM respectively, were added approximately 5 minutes before addition of the denatured TCR chains. The solution was left for ~30 minutes. The refolded TCR was dialysed in Spectrapor 1 membrane (Spectrum; Product No. 132670) against 10 L H$_2$O for 18-20 hours. After this time, the dialysis buffer was changed twice to fresh 10 mM Tris pH 8.1 (10 L) and dialysis was continued at 5° C.±3° C. for another ~8 hours.

Soluble TCR was separated from degradation products and impurities by loading the dialysed refold onto a POROS 50HQ anion exchange column and eluting bound protein with a gradient of 0-500 mM NaCl in 10 mM Tris pH 8.1 over 50 column volumes using an Akta purifier (GE Healthcare). Peak fractions were pooled and a cocktail of protease inhibitors (Calbiochem) were added. The pooled fractions were then stored at 4° C. and analysed by Coomassie-stained SDS-PAGE before being pooled and concentrated. Finally, the soluble TCR was purified and characterised using a GE Healthcare Superdex 75HR gel filtration column pre-equilibrated in PBS buffer (Sigma). The peak eluting at a relative molecular weight of approximately 50 kDa was pooled and concentrated prior to characterisation by BIAcore surface plasmon resonance analysis.

Example 3—Binding Characterisation

BIAcore Analysis

A surface plasmon resonance biosensor (BIAcore 3000™) can be used to analyse the binding of a soluble TCR to its peptide-MHC ligand. This is facilitated by producing soluble biotinylated peptide-HLA ("pHLA") complexes which can be immobilised to a streptavidin-coated binding surface (sensor chip). The sensor chips comprise four individual flow cells which enable simultaneous measurement of T-cell receptor binding to four different pHLA complexes. Manual injection of pHLA complex allows the precise level of immobilised class I molecules to be manipulated easily.

Biotinylated class I HLA-A*02 molecules were refolded in vitro from bacterially-expressed inclusion bodies containing the constituent subunit proteins and synthetic peptide, followed by purification and in vitro enzymatic biotinylation (O'Callaghan et al. (1999) *Anal. Biochem.* 266: 9-15). HLA-A*02-heavy chain was expressed with a C-terminal biotinylation tag which replaces the transmembrane and cytoplasmic domains of the protein in an appropriate construct. Inclusion body expression levels of ~75 mg/litre bacterial culture were obtained. The MEW light-chain or β2-microglobulin was also expressed as inclusion bodies in *E. coli* from an appropriate construct, at a level of ~500 mg/litre bacterial culture.

*E. coli* cells were lysed and inclusion bodies are purified to approximately 80% purity. Protein from inclusion bodies was denatured in 6 M guanidine-HCl, 50 mM Tris pH 8.1, 100 mM NaCl, 10 mM DTT, 10 mM EDTA, and was refolded at a concentration of 30 mg/litre heavy chain, 30 mg/litre β2m into 0.4 M L-Arginine, 100 mM Tris pH 8.1, 3.7 mM cystamine dihydrochloride, 6.6 mM cysteamine hydrochloride, 4 mg/L of the MAGE-3 EVDPIGHLY peptide required to be loaded by the HLA-A*01 molecule, by addition of a single pulse of denatured protein into refold buffer at <5° C. Refolding was allowed to reach completion at 4° C. for at least 1 hour.

Buffer was exchanged by dialysis in 10 volumes of 10 mM Tris pH 8.1. Two changes of buffer were necessary to reduce the ionic strength of the solution sufficiently. The protein solution was then filtered through a 1.5 μm cellulose acetate filter and loaded onto a POROS 50HQ anion exchange column (8 ml bed volume). Protein was eluted with a linear 0-500 mM NaCl gradient in 10 mM Tris pH 8.1 using an Akta purifier (GE Healthcare). HLA-A*02-peptide complex eluted at approximately 250 mM NaCl, and peak fractions were collected, a cocktail of protease inhibitors (Calbiochem) was added and the fractions were chilled on ice.

Biotin-tagged pHLA molecules were buffer exchanged into 10 mM Tris pH 8.1, 5 mM NaCl using a GE Healthcare fast desalting column equilibrated in the same buffer. Immediately upon elution, the protein-containing fractions were chilled on ice and protease inhibitor cocktail (Calbiochem) was added. Biotinylation reagents were then added: 1 mM biotin, 5 mM ATP (buffered to pH 8), 7.5 mM MgCl$_2$, and 5 μg/ml BirA enzyme (purified according to O'Callaghan et al. (1999) *Anal. Biochem.* 266: 9-15). The mixture was then allowed to incubate at room temperature overnight.

The biotinylated pHLA-A*02 molecules were purified using gel filtration chromatography. A GE Healthcare Superdex 75 HR 10/30 column was pre-equilibrated with filtered PBS and 1 ml of the biotinylation reaction mixture was loaded and the column was developed with PBS at 0.5 ml/min using an Akta purifier (GE Healthcare). Biotinylated pHLA-A*02 molecules eluted as a single peak at approximately 15 ml. Fractions containing protein were pooled, chilled on ice, and protease inhibitor cocktail was added. Protein concentration was determined using a Coomassie-binding assay (PerBio) and aliquots of biotinylated pHLA-A*01 molecules were stored frozen at −20° C.

Such immobilised complexes are capable of binding both T-cell receptors and the coreceptor CD8αα, both of which may be injected in the soluble phase. The pHLA binding properties of soluble TCRs are observed to be qualitatively and quantitatively similar if the TCR is used either in the soluble or immobilised phase. This is an important control for partial activity of soluble species and also suggests that biotinylated pHLA complexes are biologically as active as non-biotinylated complexes.

The BIAcore 3000™ surface plasmon resonance (SPR) biosensor measures changes in refractive index expressed in response units (RU) near a sensor surface within a small flow cell, a principle that can be used to detect receptor ligand interactions and to analyse their affinity and kinetic parameters. The BIAcore experiments were performed at a temperature of 25° C., using PBS buffer (Sigma, pH 7.1-7.5) as the running buffer and in preparing dilutions of protein samples. Streptavidin was immobilised to the flow cells by standard amine coupling methods. The pHLA complexes were immobilised via the biotin tag. The assay was then performed by passing soluble TCR over the surfaces of the different flow cells at a constant flow rate, measuring the SPR response in doing so.

Equilibrium Binding Constant

The above BIAcore analysis methods were used to determine equilibrium binding constants. Serial dilutions of the disulfide linked soluble heterodimeric form of the reference MAGE-A10 TCR were prepared and injected at constant flow rate of 5 µl min$^{-1}$ over two different flow cells; one coated with ~1000 RU of specific GLYDGMEHL HLA-A*02 complex, the second coated with ~1000 RU of non-specific complex. Response was normalised for each concentration using the measurement from the control cell. Normalised data response was plotted versus concentration of TCR sample and fitted to a non-linear curve fitting model in order to calculate the equilibrium binding constant, $K_D$. (Price & Dwek, Principles and Problems in Physical Chemistry for Biochemists ($2^{nd}$ Edition) 1979, Clarendon Press, Oxford). The disulfide linked soluble form of the reference MAGE-10 TCR (Example 2) demonstrated a $K_D$ of approximately 2.00 µM. From the same BIAcore data the T½ was approximately 0.95 s.

Kinetic Parameters

The above BIAcore analysis methods were also used to determine equilibrium binding constants and off-rates.

For high affinity TCRs (see Example 4 below) $K_D$ was determined by experimentally measuring the dissociation rate constant, $k_{off}$, and the association rate constant, $k_{on}$. The equilibrium constant $K_D$ was calculated as $k_{off}/k_{on}$.

TCR was injected over two different cells one coated with ~1000 RU of specific GLYDGMEHL HLA-A*02complex, the second coated with ~1000 RU of non-specific complex. Flow rate was set at 50 µl/min. Typically 250 µl of TCR at ~1 µM concentration was injected. Buffer was then flowed over until the response had returned to baseline or >2 hours had elapsed. Kinetic parameters were calculated using BIAevaluation software. The dissociation phase was fitted to a single exponential decay equation enabling calculation of half-life.

Example 4—Preparation of High Affinity TCRs of the Invention

Expression plasmids containing the TCR α-chain and β-chain respectively were prepared as in Example 1:

| TCR ID | Alpha Chain SEQ ID No | Beta Chain SEQ ID No |
|---|---|---|
| TCR1 (parental) | 4 | 5 |
| TCR2 | 4 | 14 |
| TCR3 | 4 | 15 |
| TCR4 | 4 | 16 |
| TCR5 | 4 | 17 |
| TCR6 | 12 | 5 |
| TCR7 | 13 | 5 |
| TCR8 | 13 | 15 |

The plasmids were transformed separately into *E. coli* strain BL21pLysS, and single ampicillin-resistant colonies grown at 37° C. in TYP (ampicillin 100 µg/ml) medium to $OD_{600}$ of ~0.6-0.8 before inducing protein expression with 0.5 mM IPTG. Cells were harvested three hours post-induction by centrifugation for 30 minutes at 4000 rpm in a Beckman J-6B. Cell pellets were lysed with 25 ml Bug Buster (Novagen) in the presence of $MgCl_2$ and DNaseI. Inclusion body pellets were recovered by centrifugation for 30 minutes at 13000 rpm in a Beckman J2-21 centrifuge. Three detergent washes were then carried out to remove cell debris and membrane components. Each time the inclusion body pellet was homogenised in a Triton buffer (50 mM Tris-HCl pH 8.0, 0.5% Triton-X100, 200 mM NaCl, 10 mM NaEDTA,) before being pelleted by centrifugation for 15 minutes at 13000 rpm in a Beckman J2-21. Detergent and salt was then removed by a similar wash in the following buffer: 50 mM Tris-HCl pH 8.0, 1 mM NaEDTA. Finally, the inclusion bodies were divided into 30 mg aliquots and frozen at −70° C. Inclusion body protein yield was quantified by solubilising with 6 M guanidine-HCl and an OD measurement was taken on a Hitachi U-2001 Spectrophotometer. The protein concentration was then calculated using the extinction coefficient.

Approximately 10 mg of TCR α chain and 10 mg of TCR β chain solubilised inclusion bodies for each TCR of the invention were diluted into 10 ml of a guanidine solution (6 M Guanidine-hydrochloride, 50 mM Tris HCl pH 8.1, 100 mM NaCl, 10 mM EDTA, 10 mM DTT), to ensure complete chain denaturation. The guanidine solution containing fully reduced and denatured TCR chains was then injected into 0.5 litre of the following refolding buffer: 100 mM Tris pH 8.1, 400 mM L-Arginine, 2 mM EDTA, 5 M Urea. The redox couple (cysteamine hydrochloride and cystamine dihydrochloride) to final concentrations of 6.6 mM and 3.7 mM respectively, were added approximately 5 minutes before addition of the denatured TCR chains. The solution was left for ~30 minutes. The refolded TCR was dialysed in Spectrapor 1 membrane (Spectrum; Product No. 132670) against 10 L $H_2O$ for 18-20 hours. After this time, the dialysis buffer was changed twice to fresh 10 mM Tris pH 8.1 (10 L) and dialysis was continued at 5° C.±3° C. for another ~8 hours.

Soluble TCR was separated from degradation products and impurities by loading the dialysed refold onto a POROS 50HQ anion exchange column and eluting bound protein with a gradient of 0-500 mM NaCl in 10 mM Tris pH 8.1 over 15 column volumes using an Akta purifier (GE Healthcare). The pooled fractions were then stored at 4° C. and analysed by Coomassie-stained SDS-PAGE before being pooled and concentrated. Finally, the soluble TCRs were purified and characterised using a GE Healthcare Superdex 75HR gel filtration column pre-equilibrated in PBS buffer (Sigma). The peak eluting at a relative molecular weight of approximately 50 kDa was pooled and concentrated prior to characterisation by BIAcore surface plasmon resonance analysis.

The affinity profiles of the thus-prepared TCRs for the MAGE-A10 epitope were assessed using the method of Example 3, and compared with the reference TCR. The results are set forth in the following table:

|  | T½ | $K_D$ (µM) |
|---|---|---|
| Reference (TCR1) | 0.95 s | 2.00 |
| TCR2 | 1.3 s | 1.51 |
| TCR3 | 2.0 s | 0.98 |
| TCR4 | 2.2 s | 0.89 |
| TCR5 | 5.5 s | 0.37 |
| TCR6 | 3.3 s | 0.34 |
| TCR7 | 4.2 s | 0.26 |
| TCR8 | 9.4 s | 0.14 |

Example 5—Transfection of T-Cells with Parental and Variant MAGE-A10 TCRs (a) Lentiviral Vector Preparation by Express-In Mediated Transient Transfection of 293T Cells A 3rd generation lentiviral packaging system was used to package lentiviral vectors containing the gene encoding the desired TCR. 293T cells were transfected with 4 plasmids (one lentiviral vector containing the TCR alpha chain-P2A-TCR beta chain single ORF gene described in Example 5c (below), and 3 plasmids containing the other components necessary to construct infective but non-replicative lentiviral particles) using Express-In mediated transfection (Open Biosystems).

For transfection one T150 flask of 293T cells in exponential growth phase was taken, with cells evenly distributed on the plate, and slightly more than 50% confluent. Express-In aliquots were brought to room temperature. 3 ml Serum-Free Medium (RPMI 1640+10 mM HEPES) were placed in a sterile 15 ml conical tube. 174 µl of Express-In Reagent were added directly into the Serum-Free Medium (this provides for a 3.6:1 weight ratio of Reagent to DNA). This was mixed thoroughly by inverting tubes 3-4 times and incubated at room temperature for 5-20 minutes.

In a separate 1.5 ml microtube was added 15 µg plasmid DNA to premixed packaging mix aliquots (containing 18 µg pRSV.REV (Rev expression plasmid), 18 µg pMDLg/p.RRE (Gag/Pol expression plasmid), 7 µg pVSV-G (VSV glycoprotein expression plasmid), usually ~22 and pipetted up and down to ensure homogeneity of the DNA mix. Approx 1 mL of Express-In/Serum-Free Medium was added to the DNA mix dropwise then pipetted up and down gently before transferring back to the remainder of the Express-In/Serum-Free Medium. The tube was inverted tube 3-4 times and incubated at room temperature for 15-30 minutes. Old culture medium was removed from the flask of cells. Express-In/medium/DNA (3 mL) complex was added directly into the bottom of an upright flask of 293T cells. Slowly, the flask was placed flat to cover the cells and very gently rocked to ensure even distribution. After 1 minute 22 ml fresh culture medium (R10+HEPES: RPMI 1640, 10% heat-inactivated FBS, 1% Pen/Strep/L-glutamine, 10 mM HEPES) was added and the flask carefully returned to the incubator. This was incubated overnight at 37° C./5% CO2. After 24 hours, the medium containing packaged lentiviral vectors was harvested.

To harvest the packaged lentiviral vectors, the cell culture supernatant was filtered through a 0.45 micron nylon syringe filter, the culture medium centrifuged at 10,000 g for 18 hours (or 112,000 g for 2 hours), most of the supernatant removed (taking care not to disturb the pellet) and the pellet resuspended in the remaining few mL of supernatant (usually about 2 ml from a 31 ml starting volume per tube). This was snap frozen on dry ice in 1 ml aliquots and stored at −80° C.

(b) Transduction of T Cells with Packaged Lentiviral Vectors Containing Gene of Interest Prior to transduction with the packaged lentiviral vectors, human T cells (CD8 or CD4 or both depending on requirements) were isolated from the blood of healthy volunteers. These cells were counted and incubated overnight in R10 containing 50 U/mL IL-2 at $1\times10^6$ cells per ml (0.5 mL/well) in 48 well plates with pre-washed anti-CD3/CD28 antibody-coated microbeads (Dynabeads® T cell expander, Invitrogen) at a ratio of 3 beads per cell.

After overnight stimulation, 0.5 ml of neat packaged lentiviral vector was added to the desired cells. This was incubated at 37° C./5% CO2 for 3 days. 3 days post-transduction the cells were counted and diluted to $0.5\times10^6$ cells/ml. Fresh medium containing IL-2 was added as required. Beads were removed 5-7 days post-transduction. Cells were counted and fresh medium containing IL-2 replaced or added at 2 day intervals. Cells were kept between $0.5\times10^6$ and $1\times10^6$ cells/mL. Cells were analysed by flow cytometry from day 3 and used for functional assays (e.g. ELISpot for IFNγ release, see Example 6) from day 5. From day 10, or when cells are slowing division and reduced in size, cells are frozen in aliquots of at least $4\times10^6$ cells/vial (at $1\times10^7$ cells/ml in 90% FBS/10% DMSO) for storage.

(c) Parental TCR Gene for T-Cell Transfection by Methods (a) and (b) Above

FIG. 7 is a DNA sequence (SEQ ID No: 18) encoding the parental MAGE A10 TCR (codon-optimised for maximal human cell expression). It is a full length alpha chain—Porcine teschovirus-1 2A—full length beta chain single open reading frame construct. The 2A sequence is underlined, and is preceded by nucleotides encoding a furin cleavage site to assist proteolytic removal of the 2A sequence (discussed further below in relation to FIG. 8 (SEQ ID No: 19). Peptide bond skipping during protein translation of the mRNA at the 3' end of the 2A sequence produces two proteins: 1) alpha TCR chain-2A fusion, 2) beta TCR chain.

FIG. 8 is the amino acid sequence (SEQ ID No: 19) corresponding to FIG. 7. In FIG. 8:
- M1-Q22 is a leader sequence which is removed on maturation of the parental alpha chain TCR;
- Q23-S274 corresponds to the parental alpha chain sequence;
- Q23-N247 corresponds to the parental alpha chain extracellular domain;
- L248-T268 is the alpha chain transmembrane region of the mature TCR;
- L269-S274 is the alpha chain intracellular region of the mature TCR;
- R277-R280 is the furin cleavage site to assist proteolytic removal, in the Golgi apparatus, of the P2A sequence A285-P303;
- G275, S276, S281 to G284, are flexible linkers allowing full function of the furin cleavage and P2A sequences;
- R304-V323 is a leader sequence which is removed on maturation of the parental beta chain TCR;
- N324-G612 corresponds to the parental beta chain sequence;
- N324-E583 corresponds to the parental beta chain extracellular domain;
- I584-V605 is the beta chain transmembrane region of the mature TCR;
- K606-G612 is the beta chain intracellular region of the mature TCR.

(d) T-Cells Transfected with Parental and High Affinity MAGE-A10 TCRs

Following the procedures described in (a) and (b) above, the parental MAGE A10 alpha-2A-beta TCR gene (SEQ ID No: 18 (FIG. 7)) was inserted into the pELNSxv lenti vector using the NheI and SalI restriction sites unique to both DNA constructs, and transfected T-cells created.

Similarly, T-cells may be created by transfection with genes which may comprise a sequence encoding an alpha chain variable domain having one of SEQ ID Nos: 2, 6 or 7 and which is associated with a sequence encoding a beta chain variable domain SEQ ID Nos: 3, 8, 9, 10 or 11.

Example 6—Activation of MAGE A10 TCR Engineered T Cells

The following assay was carried out to demonstrate the activation of TCR-transduced cytotoxic T lymphocytes (CTLs) in response to tumour cell lines. IFN-γ production, as measured using the ELISPOT assay, was used as a read-out for cytotoxic T lymphocyte (CTL) activation.
ELISPOTs
Reagents Assay media: 10% FCS (Gibco, Cat #2011-09), 88% RPMI 1640 (Gibco, Cat #42401), 1% glutamine (Gibco Cat #25030) and 1% penicillin/streptomycin (Gibco Cat #15070-063).

Wash buffer: 0.01M PBS/0.05% Tween 20

PBS (Gibco Cat #10010)

The Human IFNγ ELISPOT kit (BD Bioscience; Cat #551849) containing capture and detection antibodies and Human IFN-γ PVDF ELISPOT 96 well plates, with associated AEC substrate set (BD Bioscience, Cat #551951)

Methods

Target Cell Preparation

The target cells used in this method were natural epitope-presenting cells: A375 human melanoma cells which are both HLA-A2+ MAGE A10+. HCT116 human colon cancer, which are HLA-A2+ MAGE A10-, were used as a negative control. Sufficient target cells (50,000 cells/well) were washed by centrifugation three times at 1200 rpm, 10 min in a Megafuge® 1.0 (Heraeus). Cells were then re-suspended in assay media at $10^6$ cells/ml.

Effector Cell Preparation

The effector cells (T cells) used in this method were peripheral blood lymphocytes (PBL), obtained by negative selection using CD14 and CD25 microbead kits (Miltenyi Biotech Cat #130-050-201 and 130-092-983 respectively) from freshly isolated peripheral blood mononuclear cells (PBMC) from the venous blood of healthy volunteers. Cells were stimulated with antiCD3/CD28 coated beads (Dynabeads® T cell expander, Invitrogen), transduced with lentivirus carrying the gene encoding the full TCR of interest (based on the construct described in Example 5) and expanded in assay media containing 50 U/mL IL-2 until between 10 and 13 days post transduction. These cells were then placed in assay media prior to washing by centrifugation at 1200 rpm, 10 min in a Megafuge® 1.0 (Heraeus). Cells were then re-suspended in assay media at a 4× the final required concentration.

Plates were prepared as follows: 100 μL anti-IFN-γ capture antibody was diluted in 10 ml sterile PBS per plate. 100 μL of the diluted capture antibody was then dispensed into each well. The plates were then incubated overnight at 4° C. Following incubation the plates were washed (programme 1, plate type 2, Ultrawash Plus 96-well plate washer; Dynex) to remove the capture antibody. Plates were then blocked by adding 200 μL of assay media to each well and incubated at room temperature for two hours. The assay media was then washed from the plates (programme 1, plate type 2, Ultrawash Plus 96-well plate washer, Dynex) and any remaining media was removed by flicking and tapping the ELISPOT plates on a paper towel.

The constituents of the assay were then added to the ELISPOT plate in the following order:

50 μL of target cells $10^6$ cells/ml (giving a total of 50,000 target cells/well)

50 μL media (assay media)

50 μL effector cells (20,000 TCR-transduced PBL cells/well)

The plates were then incubated overnight (37° C./5% $CO_2$). The next day the plates were washed three times (programme 1, plate type 2, Ultrawash Plus 96-well plate washer, Dynex) with wash buffer and tapped dry on paper towel to remove excess wash buffer. 100 μl of primary detection antibody was then added to each well. The primary detection antibody was diluted into 10 mL of dilution buffer (the volume required for a single plate) using the dilution specified in the manufacturer's instructions. Plates were then incubated at room temperature for at least 2 hours prior to being washed three times (programme 1, plate type 2, Ultrawash Plus 96-well plate washer, Dynex) with wash buffer; excess wash buffer was removed by tapping the plate on a paper towel.

Secondary detection was performed by adding 100 μL of diluted streptavidin-HRP to each well and incubating the plate at room temperature for 1 hour. The streptavidin-HRP was diluted into 10 mL dilution buffer (the volume required for a single plate), using the dilution specified in the manufacturer's instructions. The plates were then washed three times (programme 1, plate type 2, Ultrawash Plus 96-well plate washer, Dynex) with wash buffer and tapped on paper towel to remove excess wash buffer. Plates were then washed twice with PBS by adding 200 μL to each well, flicking the buffer off and tapping on a paper towel to remove excess buffer. No more than 15 min prior to use, one drop (20 uL) of AEC chromogen was added to each 1 ml of AEC substrate and mixed. 10 ml of this solution was prepared for each plate; 100 μL was added per well. The plate was then protected from light using foil, and spot development monitored regularly, usually occurring within 5-20 min. The plates were washed in tap water to terminate the development reaction, and shaken dry prior to their disassembly into three constituent parts. The plates were then allowed to dry at room temperature for at least 2 hours prior to counting the spots using an Immunospot® Plate reader (CTL; Cellular Technology Limited).

Results

IFNγ release by activated TCR-transduced T cells in response to a variety of AFP-positive and control tumour cell lines was tested by ELISPOT assay (as described above). The number of ELISPOT spots observed in each well was plotted using Graph Pad Prism®.

CD4+, CD8+ or mixed CD4+/CD8+ T cells expressing one of TCR Nos. 1-8 were incubated with MAGE A10+ HLA:A2+ tumour cell line A375 or with MAGE A10+ HLA:A2+ HCT116 tumour cell line. A sample containing no T cells and a sample of non-transduced T cells were used as controls.

| TCR no | TCR alpha variable domain SEQ ID No: | TCR beta variable domain SEQ ID No: |
| --- | --- | --- |
| 1 | 2 | 3 |
| 2 | 2 | 8 |
| 3 | 2 | 9 |
| 4 | 2 | 10 |
| 5 | 2 | 11 |
| 6 | 6 | 3 |
| 7 | 7 | 3 |
| 8 | 7 | 9 |

FIG. 9 demonstrates that T cells transduced with the TCRs described in the table above are activated in response to MAGE A10 positive tumour cells. Normal hepatocytes (HCT116) are MAGE A10 negative and do not induce activation of T cells transduced with MAGE A10 TCRs. Therefore, the MAGE A10 TCRs of the invention selectively recognise MAGE A10 presenting cells.

Example 7—Identification of the Binding Motif by Substitution with all Alternative Amino Acids Variants of the native MAGE-A10 peptide were obtained in which the amino acid residue at each position was sequentially replaced with all 19 alternative naturally-occurring amino acid, such that 171 peptides were prepared in total. The native and amino-acid substituted peptides were pulsed on to antigen presenting cells, and interferon γ (IFNγ) production, as measured using the ELISpot assay, used as a read-out for the activation of T cells transduced with TCR5. Essential positions were defined by a greater than 50% reduction in T cell activity relative to the native peptide.

ELISpot assays were carried as described in Example 6.

The tolerated residues at each position of the peptide are shown below. Underlined amino acids represent the native residue at the corresponding position in the peptide.

| Position | Tolerated residues |
|---|---|
| 1 | G LTVMQISACNFYPDEHKRW |
| 2 | L TVMQISACGNF |
| 3 | Y FW |
| 4 | D CAV |
| 5 | G ASTLP |
| 6 | M P |
| 7 | E Q |
| 8 | H LMRQC |
| 9 | M LIVTAFC |

It is therefore apparent that the MAGE A10 TCR5 makes contact with at least Y3 and 7E of the GLYDGMEHL peptide (SEQ ID no: 1) when in complex with HLA-A*02 on the surface of antigen presenting cells.

The invention is further described by the following numbered paragraphs:

1. A T cell receptor (TCR) having the property of binding to GLYDGMEHL (SEQ ID No: 1) in complex with HLA-A*02 with a dissociation constant of from about 0.05 μM to about 10.0 μM when measured with surface plasmon resonance at 25° C. and at a pH between 7.1 and 7.5 using a soluble form of the TCR, wherein the TCR comprises a TCR alpha chain variable domain and a TCR beta chain variable domain, and wherein the TCR variable domains form contacts with at least residues Y3 and E7 of GLYDGMEHL (SEQ ID No: 1).

2. A TCR according to paragraph 1, which is an alpha-beta heterodimer, having an alpha chain TRAC constant domain sequence and a beta chain TRBC1 or TRBC2 constant domain sequence.

3. A TCR of paragraph 2, wherein the alpha and beta chain constant domain sequences are modified by truncation or substitution to delete the native disulfide bond between Cys4 of exon 2 of TRAC and Cys2 of exon 2 of TRBC1 or TRBC2.

4. A TCR of paragraph 2 or paragraph 3, wherein the alpha and beta chain constant domain sequences are modified by substitution of cysteine residues for Thr 48 of TRAC and Ser 57 of TRBC1 or TRBC2, the said cysteines forming a disulfide bond between the alpha and beta constant domains of the TCR.

5. A TCR of paragraph 1, which is in single chain format of the type Vα-L-Vβ, L-Vα, Vα-Cα-L-Vβ, or Vα-L-Vβ-Cβ, wherein Vα and Vβ are TCR α and β variable regions respectively, Cα and Cβ are TCR α and β constant regions respectively, and L is a linker sequence.

6. A TCR of any preceding paragraph, which is associated with a detectable label, a therapeutic agent or a PK modifying moiety.

7. A TCR of any preceding paragraph, wherein the alpha chain variable domain comprises an amino acid sequence that has at least 80% identity to the sequence of amino acid residues 1-111 of SEQ ID No: 4 and has the following mutation:

| Q31 | A or S |
|---|---| with reference to the numbering shown in SEQ ID No: 4, and/or the beta chain variable domain comprises an amino acid sequence that has at least 80% identity to the sequence of amino acid residues 1-111 of SEQ ID No: 5 and has at least one of the following mutations:

| E30 | D |
|---|---|
| G51 | S, A or F | with reference to the numbering shown in SEQ ID No: 5.

8. A TCR of any preceding paragraph, wherein the alpha chain variable domain comprises the amino acid sequence of amino acid residues 1-111 of SEQ ID No: 6 or 12 or an amino acid sequence in which amino acid residues 1-26, 33-49, 55-89 and 94-111 thereof have at least 90% or 95% identity to the sequence of amino acid residues 1-26, 33-49, 55-89 and 94-111 respectively of SEQ ID No: 6 or 12 and in which amino acid residues 27-32, 50-54 and 90-93 have at least 90% or 95% identity to the sequence of amino acid residues 27-32, 50-54 and 90-93 respectively of SEQ ID No: 6 or 12.

9. A TCR of any one of paragraphs 1-7, wherein the alpha chain variable domain comprises the amino acid sequence of amino acid residues 1-111 of SEQ ID No: 7 or 13 or an amino acid sequence in which amino acid residues 1-26, 33-49, 55-89 and 94-111 thereof have at least 90% or 95% identity to the sequence of amino acid residues 1-26, 33-49, 55-89 and 94-111 respectively of SEQ ID No: 7 or 13 and in which amino acid residues 27-32, 50-54 and 90-93 have at least 90% or 95% identity to the sequence of amino acid residues 27-32, 50-54 and 90-93 respectively of SEQ ID No: 7 or 13.

10. A TCR of any preceding paragraph, wherein in the alpha chain variable domain the sequence of
(i) amino acid residues 1-26 thereof has (a) at least 90% identity to the sequence of amino acid residues 1-26 of SEQ ID No: 4 or (b) has one, two or three amino acid residues inserted or deleted relative to the sequence of (a);
(ii) amino acid residues 27-32 is DRGSQS, DRGSAS or DRGSSS;
(iii) amino acid residues 33-49 thereof has (a) at least 90% identity to the sequence of amino acid residues 33-49 of SEQ ID NO: 4 or (b) has one, two or three amino acid residues inserted or deleted relative to the sequence of (a);
(iv) amino acid residues 50-54 is IYSNG
(v) amino acid residues 55-89 thereof has at least 90% identity to the sequence of amino acid residues 55-89 of SEQ ID No: 4 or has one, two or three insertions, deletions or substitutions relative thereto;
(vi) amino acids 90-93 is AVRG; and
(vii) amino acid residues 94-111 thereof has at least 90% identity to the sequence of amino acid residues 94-111 of SEQ ID No: 4 or has one, two or three insertions, deletions or substitutions relative thereto.

11. A TCR of any preceding paragraph, wherein the beta chain variable domain comprises the amino acid sequence of SEQ ID No: 8 or 14 or an amino acid sequence in which amino acid residues 1-26, 32-48, 54-90 and 96-111 thereof have at least 90% or 95% identity to the sequence of amino acid residues 1-26, 32-48, 54-90 and 96-111 respectively of SEQ ID No: 8 or 14 and in which amino acid residues 27-31, 49-53 and 91-95 have at least 90% or 95% identity to the sequence of amino acid residues 27-31, 49-53 and 91-95 respectively of SEQ ID No: 8 or 14.

12. A TCR of any one of paragraphs 1-10, wherein the beta chain variable domain comprises the amino acid sequence of SEQ ID No: 9 or 15 or an amino acid sequence in which amino acid residues 1-26, 32-48, 54-90 and 96-111 thereof have at least 90% or 95% identity to the sequence of amino acid residues 1-26, 32-48, 54-90 and 96-111 respectively of SEQ ID No: 9 or 15 and in which amino acid residues 27-31, 49-53 and 91-95 have at least 90% or 95% identity to the sequence of amino acid residues 27-31, 49-53 and 91-95 respectively of SEQ ID No: 9 or 15.

13. A TCR of any one of paragraphs 1-10, wherein the beta chain variable domain comprises the amino acid sequence of SEQ ID No: 10 or 16 or an amino acid sequence in which amino acid residues 1-26, 32-48, 54-90 and 96-111 thereof have at least 90% or 95% identity to the sequence of amino acid residues 1-26, 32-48, 54-90 and 96-111 respectively of SEQ ID No: 10 or 16 and in which amino acid residues 27-31, 49-53 and 91-95 have at least 90% or 95% identity to the sequence of amino acid residues 27-31, 49-53 and 91-95 respectively of SEQ ID No: 10 or 16.

14. A TCR of any one of paragraphs 1 to 10, wherein the beta chain variable domain comprises the amino acid sequence of SEQ ID No: 11 or 17 or an amino acid sequence in which amino acid residues 1-26, 32-48, 54-90 and 96-111 thereof have at least 90% or 95% identity to the sequence of amino acid residues 1-26, 32-48, 54-90 and 96-111 respectively of SEQ ID No: 11 or 17 and in which amino acid residues 27-31, 49-53 and 91-95 have at least 90% or 95% identity to the sequence of amino acid residues 27-31, 49-53 and 91-95 respectively of SEQ ID No: 11 or 17.

15. A TCR according to any preceding paragraph, wherein in the beta chain variable domain the sequence of
  (i) amino acid residues 1-26 thereof has (a) at least 90% identity to the amino acid sequence of residues 1-26 of SEQ ID No: 5 or (b) has one, two or three amino acid residues inserted or deleted relative to the sequence of (a);
  (ii) amino acid residues 27-31 is MNHEY or MNHDY;
  (iii) amino acid residues 32-48 thereof has (a) at least 90% identity to the sequence of amino acid residues 32-48 of SEQ ID NO: 5 or (b) has one, two or three amino acid residues inserted or deleted relative to the sequence of (a);
  (iv) amino acid residues 49-53 is SVGEG, SVSEG, SVAEG or SVFEG;
  (v) amino acid residues 54-90 thereof has (a) at least 90% identity to the sequence of amino acid residues 54-90 of SEQ ID NO: 5 or (b) has one, two or three amino acid residues inserted or deleted relative to the sequence of (a);
  (vi) amino acids 91-95 is CASSF;
  (vii) amino acid residues 96-111 thereof has at least 90% identity to the sequence of amino acid residues 96-111 of SEQ ID No: 5 or has one, two or three insertions, deletions or substitutions relative thereto.

16. Nucleic acid encoding a TCR of any one of the preceding paragraphs.

17. An isolated or non-naturally occurring cell, especially a T-cell, presenting a TCR of any one of paragraphs 1 to 15.

18. A cell harbouring
  (a) a TCR expression vector which comprises nucleic acid of paragraph 16 in a single open reading frame, or two distinct open reading frames encoding the alpha chain and the beta chain respectively; or
  (b) a first expression vector which comprises nucleic acid encoding the alpha chain of a TCR of any of paragraphs 1 to 15, and a second expression vector which comprises nucleic acid encoding the beta chain of a TCR of any of paragraphs 1 to 15.

19. A pharmaceutical composition comprising a TCR of any one of paragraphs 1 to 15, nucleic acid of paragraph 16 or a cell of paragraph 17 or paragraph 18, together with one or more pharmaceutically acceptable carriers or excipients.

20. The TCR of any one of paragraphs 1 to 15, nucleic acid of paragraph 16 or cell of paragraph 17 or paragraph 18 for use in medicine.

21. The TCR, nucleic acid or cell for use of paragraph 20, for use in a method of treating cancer.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. An isolated non-naturally occurring recombinant T cell receptor (TCR) having the property of binding to GLYDGMEHL (SEQ ID No: 1) in complex with HLA-A*02 with a dissociation constant of from about 0.05 μM to about 10.0 μM when measured with surface plasmon resonance at 25° C. and at a pH between 7.1 and 7.5 using a soluble form of the TCR, wherein:
the TCR comprises a TCR alpha chain variable domain and a TCR beta chain variable domain, and
the TCR variable domains form contacts with at least residues Y3 and E7 of GLYDGMEHL (SEQ ID No: 1), and
the amino acid sequence of the TCR alpha chain variable domain is at least 98% identical to SEQ ID NO: 4.

2. The isolated non-naturally occurring recombinant TCR of claim 1, wherein the amino acid sequence of the TCR alpha chain variable domain is at least 99% identical to SEQ ID NO: 4.

3. The isolated non-naturally occurring recombinant TCR of claim 1, wherein the amino add sequence of the TCR alpha chain variable domain is set forth by SEQ ID NO: 4.

4. An isolated non-naturally occurring recombinant T cell receptor (TCR) having the property of binding to GLYDGMEHL (SEQ ID No: 1) in complex with HLA-A*02 with a dissociation constant of from about 0.05 μM to about 10.0 μM when measured with surface plasmon resonance at 25° C. and at a pH between 7.1 and 7.5 using a soluble form of the TCR, wherein:
the TCR comprises a TCR alpha chain variable domain and a TCR beta chain variable domain, and
the TCR variable domains form contacts with at least residues Y3 and E7 of GLYDGMEHL (SEQ ID No: 1), and
the amino acid sequence of the TCR beta chain variable domain is at least 98% identical to SEQ ID NO: 17.

5. The isolated non-naturally occurring recombinant TCR of claim 4, wherein the amino acid sequence of the TCR beta chain variable domain is at least 99% identical to SEQ ID NO: 17.

6. The isolated non-naturally occurring recombinant TCR of claim 4, wherein the amino add sequence of the TCR beta chain variable domain is set forth by SEQ ID NO: 17.

7. The isolated non-naturally occurring recombinant TCR of claim 1, wherein the amino acid sequence of the TCR beta chain variable domain is at least 98% identical to SEQ ID NO: 17.

8. The isolated non-naturally occurring recombinant TCR of claim 2, wherein the amino acid sequence of the TCR beta chain variable domain is at least 99% identical to SEQ ID NO: 17.

9. The isolated non-naturally occurring recombinant TCR of claim 3, wherein the amino acid sequence of the TCR beta chain variable domain is set forth by SEQ ID NO: 17.

10. The isolated non-naturally occurring recombinant TCR of any one of claims 1-9, which is associated with a detectable label, a therapeutic agent or a pharmacokinetics (PK) modifying moiety.

11. An isolated non-naturally occurring nucleic acid encoding the TCR of any one of claims 1-9.

12. An isolated non-naturally occurring cell harboring an expression vector comprising the nucleic acid of claim 11, wherein the TCR is encoded by a single open reading frame, or two distinct open reading frames encoding the alpha chain and the beta chain respectively.

13. An isolated non-naturally occurring T-cell presenting the TCR of any one of claims 1-9.

14. A pharmaceutical composition comprising the isolated non-naturally occurring cell of claim 13, together with one or more pharmaceutically acceptable carriers or excipients.

15. A method for treating cancer in a patient comprising administering to the patient the composition of claim 14.

16. The method of claim 15, wherein the cancer is a solid tumor.

17. The method of claim 16, wherein the solid tumor is squamous cell carcinoma.

* * * * *

UNITED STATES PATENT AND TRADEMARK OFFICE
CERTIFICATE OF CORRECTION

PATENT NO. : 11,203,627 B2
APPLICATION NO. : 15/480103
DATED : December 21, 2021
INVENTOR(S) : Conor Hayes et al.

Page 1 of 2

It is certified that error appears in the above-identified patent and that said Letters Patent is hereby corrected as shown below:

In the Claims

Claim 1, last line, please replace:
"at least 98% identical to SEQ ID NO: 4"
With:
-- at least 98% identical to amino acid residues 1-111 of SEQ ID NO: 4 --

Claim 2, last two lines, please replace:
"at least 99% identical to SEQ ID NO: 4"
With:
-- at least 99% identical to amino acid residues 1-111 of SEQ ID NO: 4 --

Claim 3, last line, please replace:
"set forth by SEQ ID NO: 4"
With:
-- set forth by amino acid residues 1-111 of SEQ ID NO: 4 --

Claim 4, last line, please replace:
"at least 98% identical to SEQ ID NO: 17"
With:
-- at least 98% identical to amino acid residues 1-111 of SEQ ID NO: 17 --

Claim 5, last two lines, please replace:
"at least 99% identical to SEQ ID NO: 17"
With:
-- at least 99% identical to amino acid residues 1-111 of SEQ ID NO: 17 --

Claim 6, last line, please replace:
"set forth by SEQ ID NO: 17"

Signed and Sealed this
Twelfth Day of April, 2022

Drew Hirshfeld
*Performing the Functions and Duties of the*
*Under Secretary of Commerce for Intellectual Property and*
*Director of the United States Patent and Trademark Office*

CERTIFICATE OF CORRECTION (continued)
U.S. Pat. No. 11,203,627 B2

With:
-- set forth by amino acid residues 1-111 of SEQ ID NO: 17 --

Claim 7, last two lines, please replace:
"at least 98% identical to SEQ ID NO: 17"
With:
-- at least 98% identical to amino acid residues 1-111 of SEQ ID NO: 17 --

Claim 8, last two lines, please replace:
"at least 99% identical to SEQ ID NO: 17"
With:
-- at least 99% identical to amino acid residues 1-111 of SEQ ID NO: 17 --

Claim 9, last line, please replace:
"set forth by SEQ ID NO: 17"
With:
-- set forth by amino acid residues 1-111 of SEQ ID NO: 17 --